US010603091B2

(12) United States Patent
Oldakowska et al.

(10) Patent No.: US 10,603,091 B2
(45) Date of Patent: Mar. 31, 2020

(54) FASTENER

(71) Applicant: CURTIN UNIVERSITY OF TECHNOLOGY, Bentley, WA (AU)

(72) Inventors: Intan Camellia Watono Oldakowska, Bentley (AU); Matthew Peter Oldakowski, Bentley (AU); Philip Hobson Hardcastle, Bentley (AU); Thomas Brett Kirk, Bentley (AU)

(73) Assignee: CURTIN UNIVERSITY OF TECHNOLOGY, Western Australia (AU)

( * ) Notice: Subject to any disclaimer, the term of this patent is extended or adjusted under 35 U.S.C. 154(b) by 0 days.

(21) Appl. No.: 15/120,953

(22) PCT Filed: Feb. 24, 2015

(86) PCT No.: PCT/AU2015/000099
§ 371 (c)(1),
(2) Date: Aug. 23, 2016

(87) PCT Pub. No.: WO2015/123726
PCT Pub. Date: Aug. 27, 2015

(65) Prior Publication Data
US 2017/0065319 A1 Mar. 9, 2017

(30) Foreign Application Priority Data
Feb. 24, 2014 (AU) ................. 2014900596

(51) Int. Cl.
*A61B 17/84* (2006.01)
*A61B 17/70* (2006.01)
(Continued)

(52) U.S. Cl.
CPC .......... *A61B 17/844* (2013.01); *A61B 17/701* (2013.01); *A61B 17/7007* (2013.01);
(Continued)

(58) Field of Classification Search
CPC ... A61B 17/84; A61B 17/844; A61B 17/8685; A61B 17/70; A61B 17/701
(Continued)

(56) References Cited

U.S. PATENT DOCUMENTS 7,271 A  4/1850  Nash
65,526 A  6/1867  Andrews et al.
(Continued)

FOREIGN PATENT DOCUMENTS

CA  2334443  12/1999
CN  201719362 U  1/2011
(Continued)

OTHER PUBLICATIONS

International Preliminary Report on Patentability received in corresponding International Application No. PCT/AU2015/000099 dated Jun. 2, 2016, 8 pages.
(Continued)

*Primary Examiner* — Si Ming Ku
(74) *Attorney, Agent, or Firm* — Foley & Lardner LLP

(57) ABSTRACT

The present disclosure provides a fastener that has a body that has an axis. The body comprises a head portion and at least one body portion projecting from the head portion. The at least one body portion has an actuating surface portion and is arranged such that at least a part of the at least one body portion is urged away from the axis when an actuating member is received along the axis and urges against the actuating surface portion. The at least one body portion has a substantially flat surface portion facing away from the axis.

15 Claims, 25 Drawing Sheets

(51) Int. Cl.
  *A61B 17/80* (2006.01)
  *A61B 17/86* (2006.01)
  *F16B 19/10* (2006.01)
(52) U.S. Cl.
  CPC ...... *A61B 17/7014* (2013.01); *A61B 17/7026* (2013.01); *A61B 17/7028* (2013.01); *A61B 17/8023* (2013.01); *A61B 17/8685* (2013.01); *F16B 19/1081* (2013.01); *A61B 2017/8655* (2013.01)
(58) Field of Classification Search
  USPC ............ 606/282, 313, 326, 327; 411/49, 52, 411/57.1, 71, 271, 325
  See application file for complete search history.

(56) References Cited

U.S. PATENT DOCUMENTS

| | | | |
|---|---|---|---|
| 254,124 | A | 2/1882 | Forbes |
| 2,381,050 | A | 8/1945 | Hardinge |
| 3,431,813 | A * | 3/1969 | Johnson ................. F16B 13/04 411/61 |
| 3,693,616 | A | 9/1972 | Roaf et al. |
| 4,041,939 | A | 8/1977 | Hall |
| 4,047,524 | A | 9/1977 | Hall |
| 4,580,936 | A | 4/1986 | Francis et al. |
| 4,716,893 | A | 1/1988 | Fischer et al. |
| 4,776,851 | A | 10/1988 | Bruchman et al. |
| 5,030,220 | A | 7/1991 | Howland |
| 5,084,050 | A | 1/1992 | Draenert |
| 5,092,866 | A | 3/1992 | Breard et al. |
| 5,100,273 | A | 3/1992 | Vassiliou |
| 5,282,863 | A | 2/1994 | Burton |
| 5,375,823 | A | 12/1994 | Navas |
| 5,480,401 | A | 1/1996 | Navas |
| 5,489,210 | A | 2/1996 | Hanosh |
| 5,501,695 | A | 3/1996 | Anspach et al. |
| 5,540,688 | A | 7/1996 | Navas |
| 5,618,142 | A | 4/1997 | Sonden et al. |
| 5,628,581 | A | 5/1997 | Hintz et al. |
| 5,713,904 | A | 2/1998 | Errico et al. |
| 5,720,753 | A | 2/1998 | Sander et al. |
| 5,954,722 | A | 9/1999 | Bono |
| 6,168,597 | B1 | 1/2001 | Biedermann et al. |
| 6,290,700 | B1 | 9/2001 | Schmotzer |
| 6,299,613 | B1 | 10/2001 | Ogilvie et al. |
| 6,511,481 | B2 | 1/2003 | Von Hoffmann |
| 6,540,751 | B2 | 4/2003 | Enayati |
| 7,074,203 | B1 | 7/2006 | Johanson et al. |
| 8,043,340 | B1 | 10/2011 | Law |
| 8,105,360 | B1 | 1/2012 | Connor |
| 8,926,611 | B2 | 1/2015 | Keller |
| 9,452,003 | B2 | 9/2016 | Voor |
| 2002/0007184 | A1 | 1/2002 | Ogilvie et al. |
| 2002/0049447 | A1 | 4/2002 | Li |
| 2002/0173791 | A1 | 11/2002 | Howland |
| 2003/0144667 | A1 | 7/2003 | Enayati |
| 2004/0034353 | A1 | 2/2004 | Michelson |
| 2005/0055027 | A1 | 3/2005 | Yeung et al. |
| 2005/0101956 | A1 | 5/2005 | Simonson |
| 2005/0152766 | A1* | 7/2005 | Ballou ................. F16B 13/063 411/57.1 |
| 2006/0235410 | A1 | 10/2006 | Ralph et al. |
| 2006/0247635 | A1 | 11/2006 | Gordon et al. |
| 2007/0162002 | A1 | 7/2007 | Tornier |
| 2007/0162003 | A1 | 7/2007 | Tornier et al. |
| 2007/0162004 | A1 | 7/2007 | Tornier et al. |
| 2007/0282443 | A1 | 12/2007 | Globerman et al. |
| 2008/0183209 | A1 | 7/2008 | Robinson et al. |
| 2009/0105759 | A1 | 4/2009 | Gimbel et al. |
| 2009/0224023 | A1 | 9/2009 | Moskowitz et al. |
| 2009/0287249 | A1 | 11/2009 | Reynolds et al. |
| 2010/0036496 | A1 | 2/2010 | Yu et al. |
| 2010/0094358 | A1 | 4/2010 | Moore et al. |
| 2010/0121328 | A1* | 5/2010 | Reitzig ............. A61B 17/7059 606/71 |
| 2010/0152790 | A1 | 6/2010 | Hestad |
| 2010/0198276 | A1 | 8/2010 | Krebs et al. |
| 2010/0324558 | A1* | 12/2010 | Bickley ................ A61B 17/686 606/71 |
| 2010/0324606 | A1 | 12/2010 | Moskowitz et al. |
| 2010/0324607 | A1 | 12/2010 | Davis |
| 2011/0152935 | A1 | 6/2011 | Fortin et al. |
| 2011/0160774 | A1 | 6/2011 | Malek |
| 2011/0208312 | A1 | 8/2011 | Moskowitz et al. |
| 2011/0218571 | A1 | 9/2011 | Attia |
| 2011/0251644 | A1 | 10/2011 | Hestad et al. |
| 2011/0295320 | A1 | 12/2011 | Jackson |
| 2011/0295323 | A1 | 12/2011 | Hudgins et al. |
| 2011/0307017 | A1 | 12/2011 | Veldman et al. |
| 2011/0313461 | A1 | 12/2011 | Prevost et al. |
| 2011/0319935 | A1 | 12/2011 | Moskowitz et al. |
| 2012/0010714 | A1 | 1/2012 | Moskowitz et al. |
| 2012/0016421 | A1 | 1/2012 | Zylber et al. |
| 2012/0016422 | A1 | 1/2012 | Hua |
| 2012/0046696 | A1 | 2/2012 | Winslow et al. |
| 2012/0172934 | A1* | 7/2012 | Fisher .................. A61B 17/844 606/304 |
| 2013/0053902 | A1 | 2/2013 | Trudeau |
| 2013/0149066 | A1* | 6/2013 | Handa ..................... F16B 19/10 411/57.1 |

FOREIGN PATENT DOCUMENTS

| | | |
|---|---|---|
| DE | 42 39 716 C1 | 8/1994 |
| EP | 0 669 109 A1 | 8/1995 |
| EP | 0 919 199 B | 1/2005 |
| EP | 1 364 622 B1 | 7/2005 |
| EP | 1 952 775 A2 | 8/2008 |
| EP | 1 970 031 A2 | 9/2008 |
| EP | 2 404 563 A1 | 1/2012 |
| EP | 2 430 994 A2 | 3/2012 |
| FR | 2799949 A1 | 4/2001 |
| FR | 2827498 A1 | 1/2003 |
| GB | 2 382 304 A | 5/2003 |
| GB | 2 479 829 A | 10/2011 |
| JP | 2002-224131 A | 8/2002 |
| KR | 20080016586 A | 2/2008 |
| TW | 200843691 A | 11/2008 |
| WO | WO-95/31941 A1 | 11/1995 |
| WO | WO-98/22033 A1 | 5/1998 |
| WO | WO-01/45576 A1 | 6/2001 |
| WO | WO-2006/037384 A1 | 4/2006 |
| WO | WO-2006/045091 A2 | 4/2006 |
| WO | WO-2006/096803 | 9/2006 |
| WO | WO-2006/135511 A1 | 12/2006 |
| WO | WO-2006/136937 A2 | 12/2006 |
| WO | WO-2008/000944 A2 | 1/2008 |
| WO | WO-2008/073447 A2 | 6/2008 |
| WO | WO-2008/132322 A2 | 11/2008 |
| WO | WO-2009/062163 A1 | 5/2009 |
| WO | WO-2009/115663 A2 | 9/2009 |
| WO | WO-2010/018317 A1 | 2/2010 |
| WO | WO-2010/053785 A1 | 5/2010 |
| WO | WO-2010/091549 A1 | 8/2010 |
| WO | WO-2010/105174 A1 | 9/2010 |
| WO | WO-2010/108333 A1 | 9/2010 |
| WO | WO-2012/006064 A1 | 1/2012 |
| WO | WO-2012/024807 A1 | 3/2012 |
| WO | WO-2013/093321 A1 | 6/2013 |
| WO | WO-2014/028981 A1 | 2/2014 |

OTHER PUBLICATIONS

International Search Report in PCT/AU2015/000099 dated May 18, 2015, 4 pages.

Written Opinion of the International Searching Authority in PCT/AU2015/000099 dated May 18, 2015, 9 pages.

(56) References Cited

OTHER PUBLICATIONS

Supplementary Partial European Search Report dated Oct. 6, 2017, in corresponding European application No. 15751694.9, 12 pages.

* cited by examiner

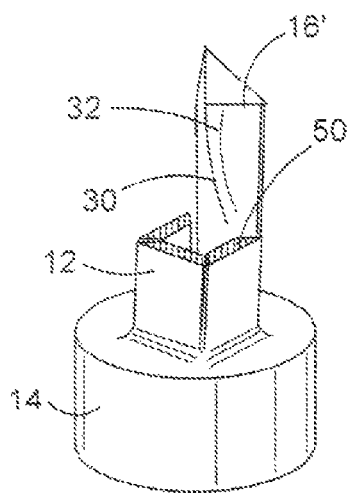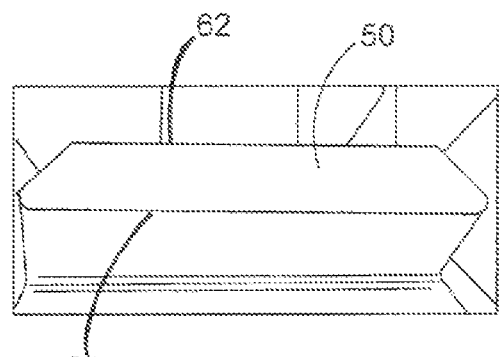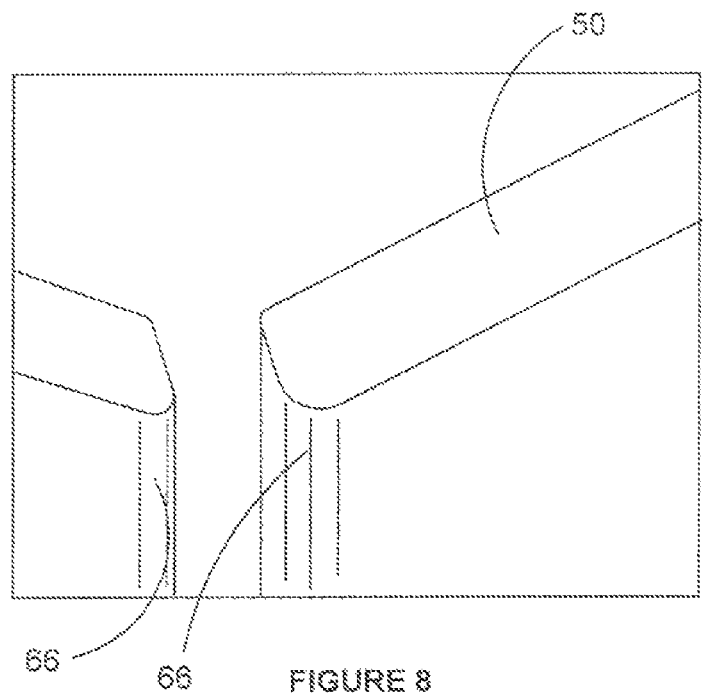

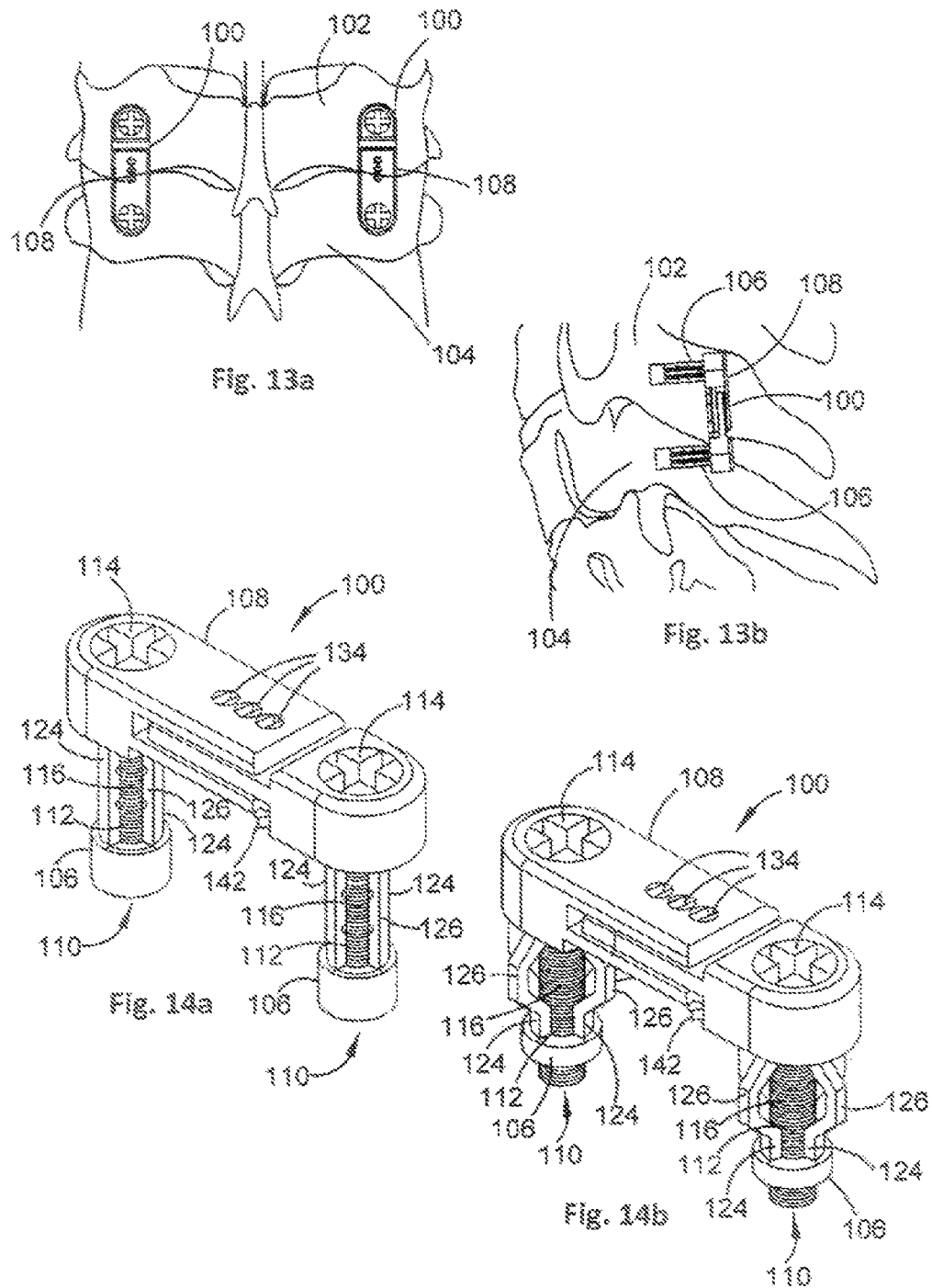

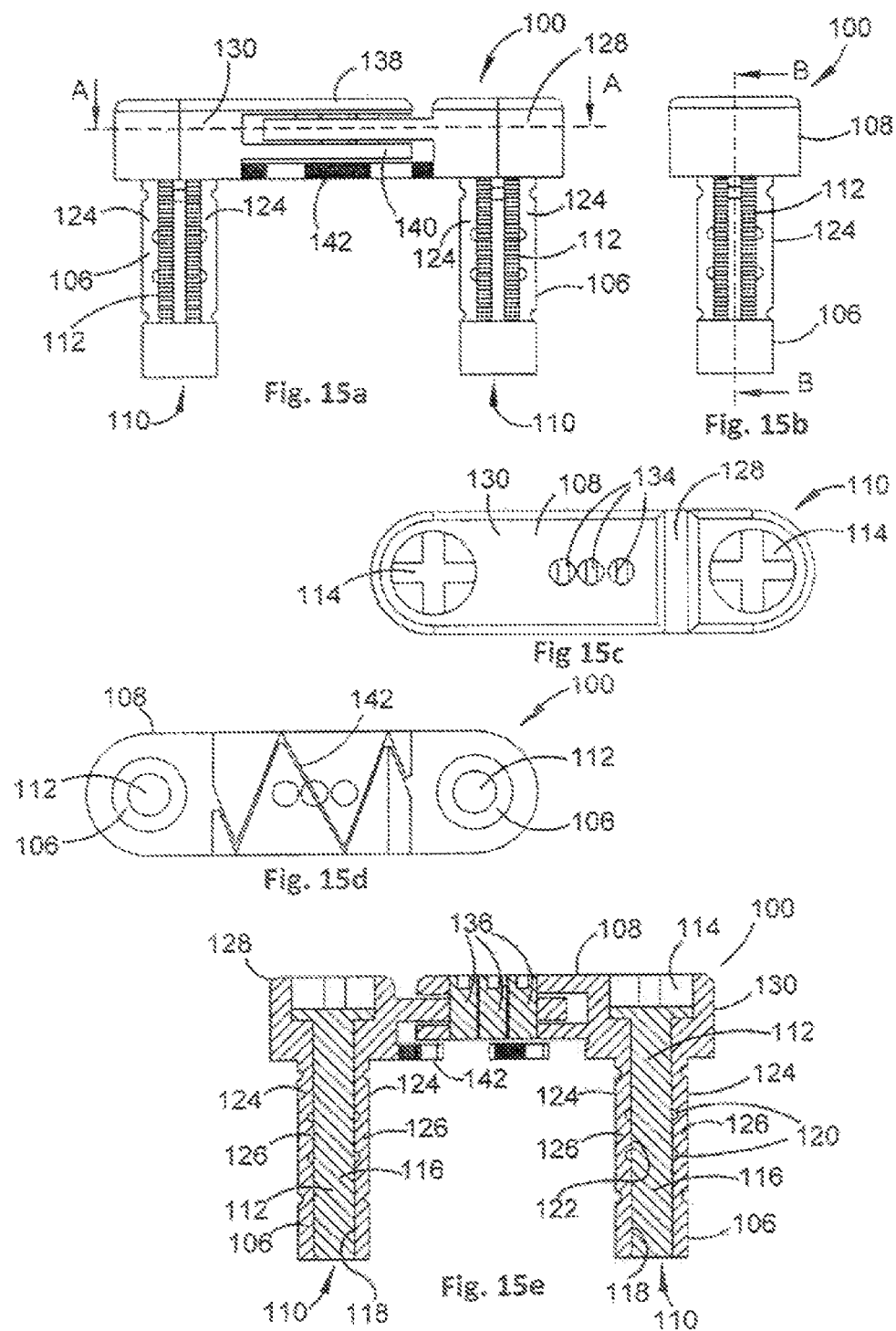

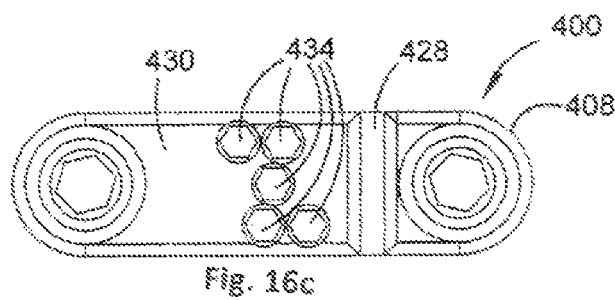
Fig. 16c
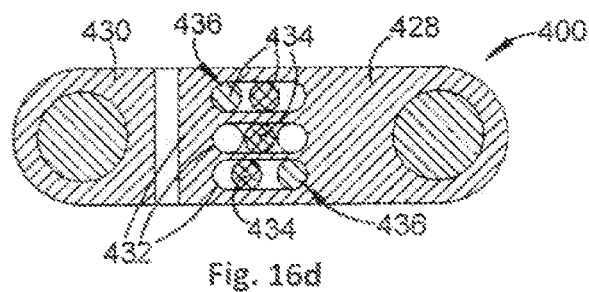
Fig. 16d
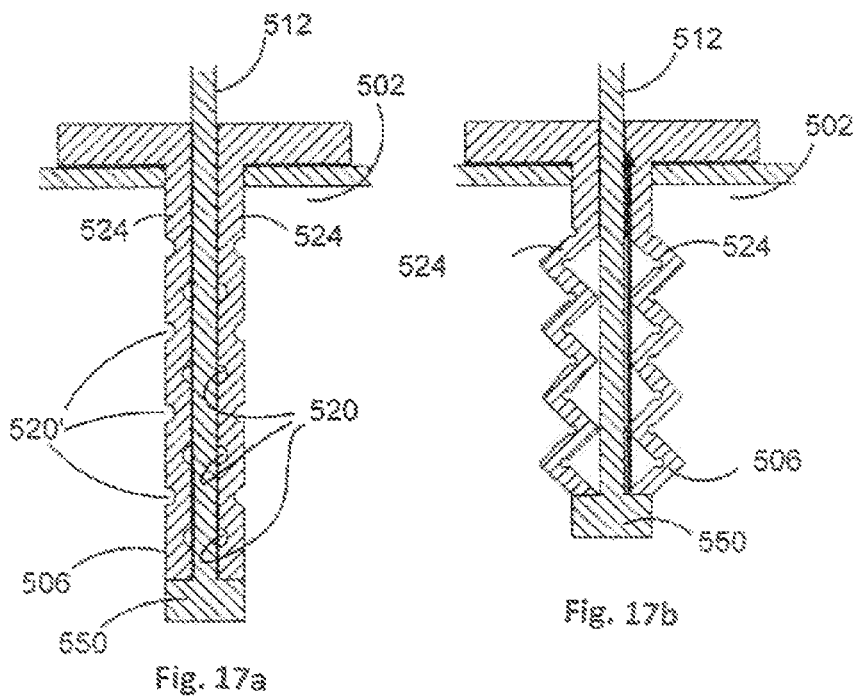
Fig. 17a
Fig. 17b

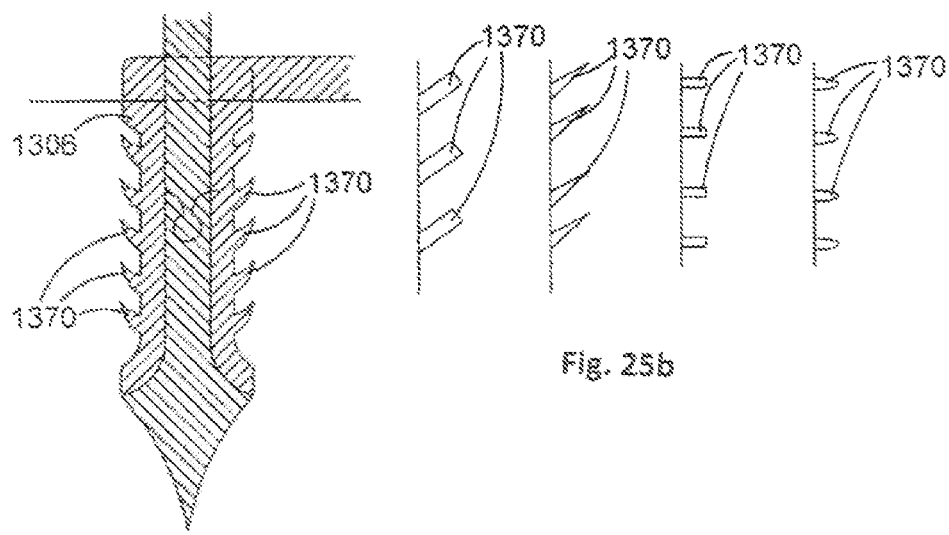
Fig. 25a
Fig. 25b
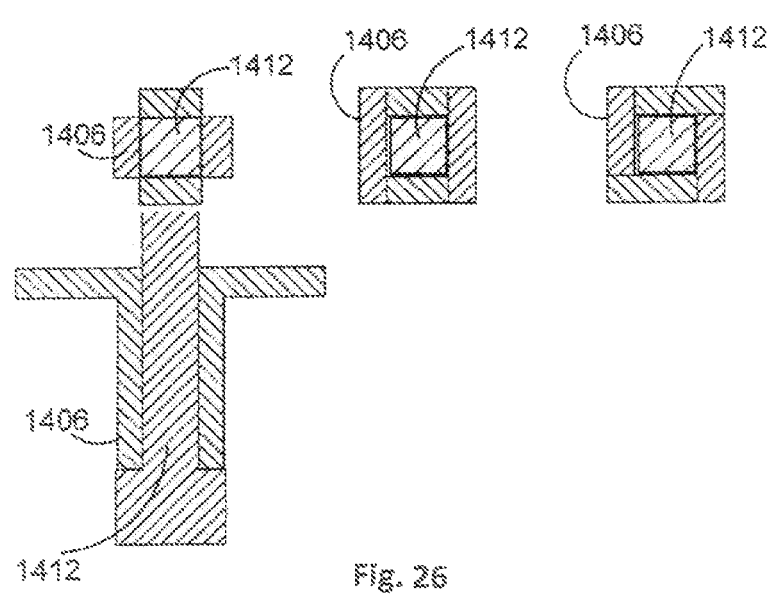
Fig. 26

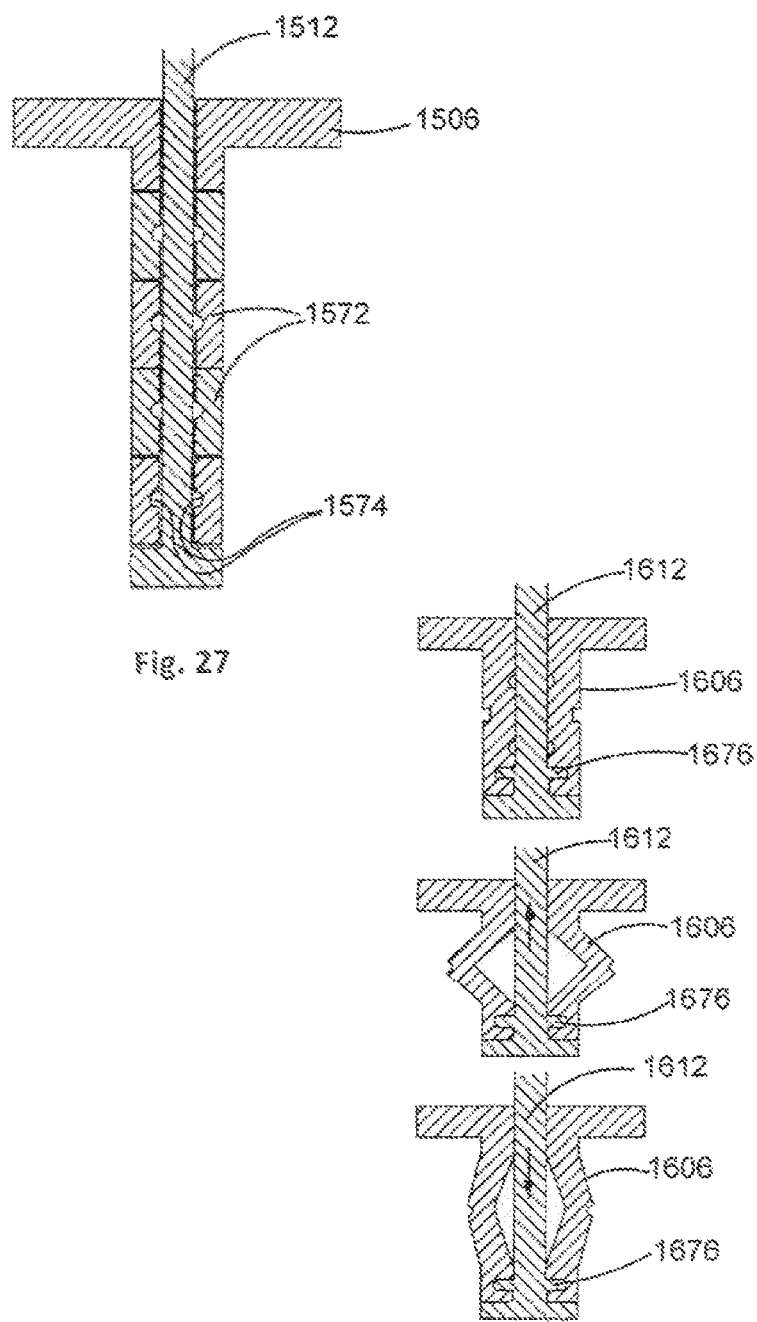

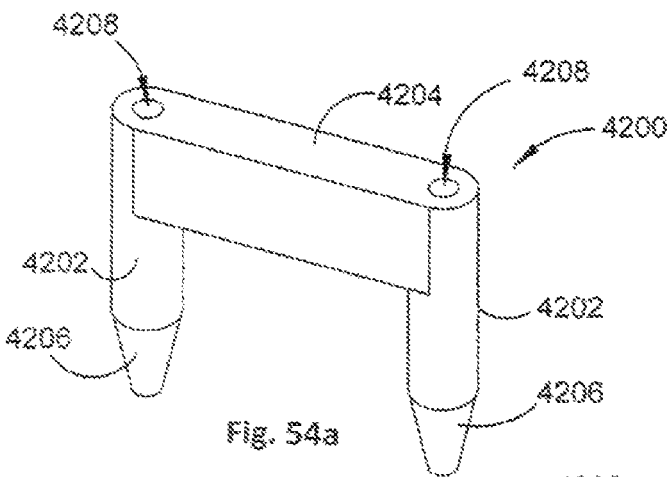
Fig. 54a
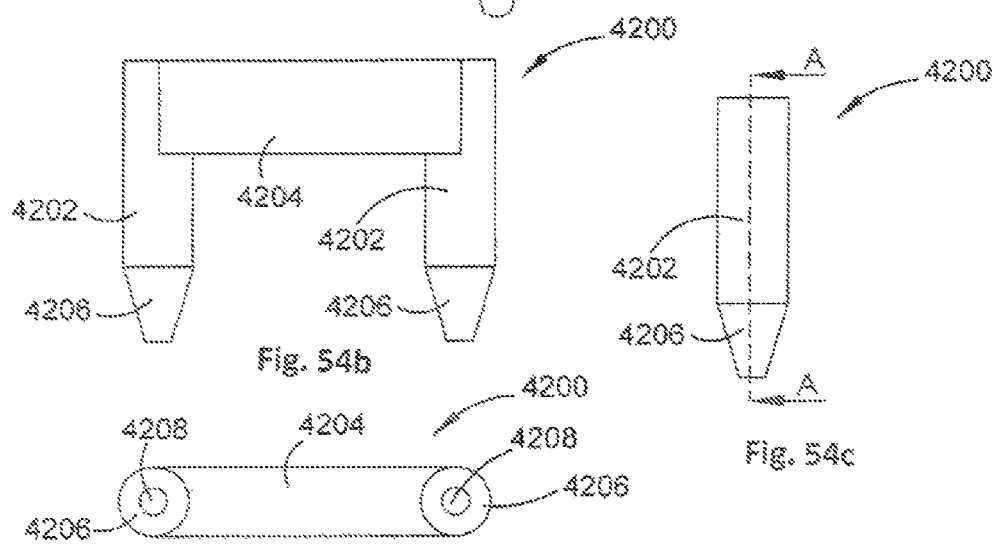
Fig. 54b
Fig. 54c
Fig. 54d
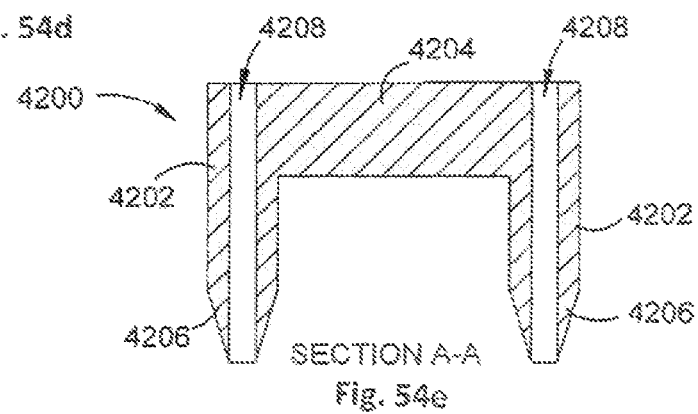
SECTION A-A
Fig. 54e

FASTENER

CROSS REFERENCE TO RELATED APPLICATIONS

The present application is a U.S. National Stage of International Application No. PCT/AU2015/000099 filed on Feb. 24, 2015, which claims the benefit of Australian Patent Application No. 2014900596 filed on Feb. 24, 2014, the entire disclosures of all of which are incorporated herein by reference.

FIELD OF THE INVENTION

The present invention relates to a fastener.

BACKGROUND OF THE INVENTION

Expandable fasteners are well known and widely used for different applications. For example, they may be used for attaching objects to other objects or masonry work. Such fasteners may include wall plugs that expand when they are fastened. However, such wall plugs are usually relatively stiff to bend and plastically deform when they expand.

Fasteners are also used in the manufacture of various types of goods. Further, fasteners are used for medical applications such as for fastening orthopaedic stabilisation devices. Such stabilisation devices may be used to stabilise the spine and may include plates or rods that are used to span affected vertebrae.

Embodiments of the present invention provide an improved fastener.

SUMMARY OF THE INVENTION

In accordance with a first aspect of the present invention, there is provided a fastener, the fastener having a body that has an axis, the body comprising:
 a head portion; and
  at least one body portion projecting from the head portion, the at least one body portion having an actuating surface and being arranged such that at least a part of the at least one body portion is urged away from the axis when an actuating member is received along the axis and urges against the actuating surface portion; the at least one body portion having a substantially flat surface portion facing away from the axis.

The at least one body portion may have a polygonal cross-sectional shape in a plane transversal to the axis.

In accordance with a second aspect of the present invention, there is provided a fastener, the fastener having a body that has an axis, the body comprising:
 a head portion; and
  at least one body portion projecting from the head portion, the at least one body portion having an actuating surface and being arranged such that at least a part of the at least one body portion is urged away from the axis when an actuating member is received along the axis and urges against the actuating surface portion; the at least one body portion having a polygonal cross-sectional shape in a plane transversal to the axis.

The at least one body portion may have a substantially flat surface portion facing away from the axis.

The following relates to optional features of the fastener in accordance with either one of the first and second aspects of the present invention.

The at least one body portion may have a cross-sectional shape that is non-uniform along at least a portion of a length of the body portion, the cross-sectional shape being such that the at least one body portion will preferentially bend outwardly at a predefined location in response to the actuating member being received.

At least a portion of the actuating surface may be oriented substantially parallel to the substantially flat surface portion.

The at least one body portion may be thinner at the predefined location relative to an adjacent region of the body portion.

The cross-sectional shape of the at least one body portion at the predefined location may be shaped so as to increase bending modulus and to allow for maximum expansion of the fastener without plastic deformation, for example by having parallel inner and outer edges. The cross-sectional shape of the at least one body portion at the predefined location may also be shaped so as to reduce stress concentration, for example by having rounded corners.

In one embodiment, the at least one body portion has a substantially trapezoidal cross-sectional shape at a base of the body. The cross-sectional shape of the at least one body portion may transition to a substantially triangular cross-sectional shape along the length of the body portion in a direction towards an upper end of the body.

In one embodiment, the cross-sectional shape of the at least one body portion becomes thinner before transitioning to the substantially triangular cross-sectional shape.

The actuating surface may be a surface of a projection that projects towards the axis of the body such that the at least one body portion is urged outwardly when the actuating member is received in the internal region and comes into contact with the projection.

In one embodiment the body is arranged to move from a contracted to an expanded configuration and the at least one body portion being one of a plurality of body portions projecting from the head portion, the body portions together having a substantially polygonal cross-sectional profile in a plane perpendicular to the axis of the body, each body portion corresponding to a respective side of the body and defining an outer portion of the body, the body portions being arranged such that, when an actuating member is received, the body portions are urged outwardly so as to move the body to the expanded configuration.

The body portions may be arranged such that, when the body is in the contracted configuration, the body portions together define a tip at the upper end of the body that can be used to form at least a portion of a bore hole or the like.

In one embodiment, the body portions are separated along at least a portion of a length of the body by a gap, the gap tapering towards the tip of the body.

The gap may extend for substantially the length of the body portions and may taper gradually along the length of the body.

In one specific embodiment the body portions together have a substantially square shaped cross-sectional profile in the plane perpendicular to the axis of the body.

The head portion may comprise an aperture, the aperture being interconnected with an internal region of the body and being arranged for receiving the actuating member.

The body may comprise a curved portion at a base thereof so as to provide a relatively smooth transition between the body and the head portion.

At least one external surface of the fastener may have a non-smooth surface, such as that provided by micro-architecture, so as to increase friction between the at least one external surface and walls of a bore hole into which the fastener is to be fastened.

The fastener may be comprise at least two body portions and may be arranged such that the at least two body portions begin expanding at different times in response to the fastener receiving an actuating member. In one embodiment, a first body portion is arranged so as to begin expanding after a second body portion has begun expanding due to an actuating member contacting the first body portion after contacting the second body portion.

In one specific embodiment that at least one body portion has an actuating surface that extends transversally to the axis of the body. For example, the actuating surface may extend substantially from a first side of at least a part of the body to an opposite second side of the fastener.

The body portion may further comprise an engaging portion, such as an engaging projection, that is arranged to engage with material into which the fastener is to be fastened, the engaging portion extending in a direction away from the axis.

The at least one body portion may comprise one or more spikes. The one or more spikes may be arranged to facilitate retaining the body portion within material into which the fastener is inserted by piercing rather than friction, thereby reducing an amount of force required to engage the fastener with the material.

The fastener may comprise the actuating member.

In accordance with a third aspect of the present invention, there is provided an orthopaedic stabilisation device comprising:

- a stabilisation member; and
- at least two legs coupled to the stabilisation member, each leg being arranged for positioning in a respective bore hole in bone, each leg comprising a fastener in accordance with the first aspect of the present invention.

The legs may be coupled to the stabilisation member prior to positioning the legs in the respective bore holes. Such an arrangement can facilitate positioning the orthopaedic stabilisation device in a stabilising position as a single unit.

It will be appreciated that the term 'single unit', as used herein, refers to a device that may comprise different components, or that may be integrally formed.

The stabilisation member may be arranged such that a length of the stabilisation member is adjustable.

At least a portion of the at least one leg may be integral to the stabilisation member.

In one embodiment, the legs are substantially parallel to one another. An orientation of at least one leg relative to the stabilisation member may be adjustable.

The stabilisation device may be arranged such that each leg can be moved from the contracted to the expanded configuration at substantially the same time.

It will be appreciated that the predefined direction may be along a curved path.

In one embodiment, a distance between at least two legs is also variable.

The stabilisation member may be arranged to be releasable engagable with a further stabilisation member.

The stabilisation device may comprise first and second stabilisation members that are coupled together. In one embodiment, the stabilisation device comprises at least three legs wherein a first and a second leg are associated with the first stabilisation member, and the second leg and a third leg are associated with the second stabilisation member.

It will be appreciated that any appropriate number of stabilisation members may be coupled together.

The stabilisation device may comprise a plurality of stabilisation members, wherein the stabilisation members are separable from one another.

BRIEF DESCRIPTION OF THE FIGURES

Embodiments of the present invention will now be described, by way of example only, with reference to the accompanying figures, in which:

FIGS. 1 to 8 show various views of a fastener in accordance with an embodiment of the present invention;

FIG. 13a is a posterior view of a portion of a spine having two orthopaedic stabilisation devices implanted therein in accordance with an embodiment of the present invention;

FIG. 13b is a sagittal view of the spine portion of FIG. 1a;

FIG. 14a is a perspective view of an orthopaedic stabilisation device in a contracted configuration in accordance with an embodiment of the present invention;

FIG. 14b is a perspective view of the orthopaedic stabilisation device of FIG. 14b in an expanded configuration;

FIG. 15a is side view of the orthopaedic stabilisation device of FIG. 14a;

FIG. 15b is a front view of the orthopaedic stabilisation device of FIG. 14a;

FIG. 15c is a top view of the orthopaedic stabilisation device of FIG. 14a;

FIG. 15d is a bottom view of the orthopaedic stabilisation device of FIG. 14a;

FIG. 15e is a cross-sectional view of section A, as indicated in FIG. 15a, of the orthopaedic stabilisation device of FIG. 14a;

FIG. 15f is a cross-sectional view of section B, as indicated in FIG. 15b, of the orthopaedic stabilisation device or FIG. 14a;

FIG. 16b is a side view of the orthopaedic stabilisation device of FIG. 16a;

FIG. 16c is a top view of the orthopaedic stabilisation device of FIG. 16a;

FIG. 16d is a cross-sectional view of section B, as indicated in FIG. 16b, of the orthopaedic stabilisation device of FIG. 16a;

FIG. 17a is a cross-sectional view of a leg of an orthopaedic stabilisation device in a contracted configuration in accordance with an embodiment of the present invention;

FIG. 17b is a cross-sectional view of the leg of FIG. 17a in an expanded configuration;

FIG. 25a is a cross-sectional view of a leg of an orthopaedic stabilisation device in accordance with an embodiment of the present invention;

FIG. 25b is a cross-sectional view of various barb configurations for the leg of FIG. 25a;

FIG. 26 shows various cross-sectional views of a leg of an orthopaedic stabilisation device in accordance with an embodiment of the present invention;

FIG. 27 is a cross-sectional view of a leg of an orthopaedic stabilisation device in accordance with an embodiment of the present invention;

FIG. 28 is a cross-sectional view of a leg of an orthopaedic stabilisation device in accordance with an embodiment of the present invention, the leg being shown to move between contracted and expanded configurations;

FIG. 35a is a posterior view of a portion of a spine showing live springs of two orthopaedic stabilisation devices implanted therein in accordance with an embodiment of the present invention;

FIG. 35b is a sagittal view of the spine portion of FIG. 35a;

FIGS. 54a to 54e show various views of an awling tool in accordance with an embodiment of the present invention;

DETAILED DESCRIPTION

Embodiments of the present invention generally relate to a fastener. The fastener may for example be used for an orthopaedic stabilisation device and this example will be described further below in detail with reference to FIGS. 13 to 52. However, a person skilled in the art will appreciate that the fastener has applications in many other fields of technology, such as in the building and manufacturing industry.

Referring initially to FIGS. 1 to 8 there is shown a fastener 10. The fastener 10 may for example be a leg, or a portion of a leg, of an orthopaedic stabilisation device 100 that will be described further below with reference to of FIGS. 13 to 52. Alternatively, the fastener 10 may be portion of another device that may or may not be used for orthopaedic purposes.

The fastener 10 comprises an elongate body 12 and a head 14 to which the body 12 is coupled. In this example the body 12 and the head 14 are integrally formed. The fastener 10 may be formed from any appropriate material including titanium or suitable plastics materials.

Figure 1:
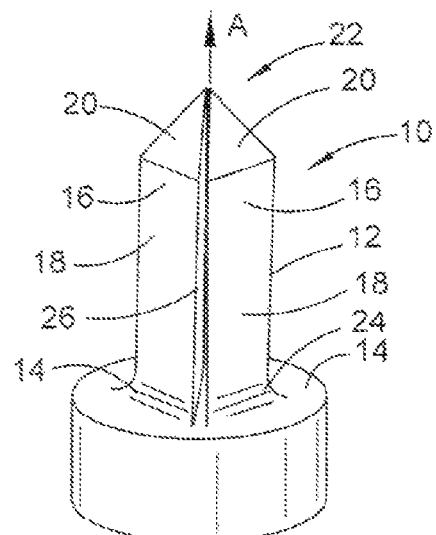

The fastener 10 is arranged to move from a contracted configuration (as shown in FIG. 1) to an expanded configuration (not shown). In the expanded configuration, body portions 16 of the body 12 move outwardly, thereby facilitating fastening the fastener 10 in a bore hole.

In this example, the body 12 has a generally obelisk-like shape. The obelisk-like shape is provided by four body portions 16, each having a substantially rectangular first external surface 18 that extends generally along a longitudinal axis A of the body 12, and a substantially triangular second external surface 20 that tapers towards the longitudinal axis A of the body 12 such that respective apices of the second external surfaces 20 meet at a first end 22 of the body 12. A curved portion 24 at a lower end of each body portion 16 provides a relatively smooth transition between the body 12 and the head 14.

The first and second external surfaces 18, 20 may have a non-smooth surface, such as that provided by micro-architecture, so as to increase friction between the first and second external surfaces 18, 20 and the walls of the bore hole.

Due to the obelisk-like shape of the body 12, the upper pyramidal structure can function as an awling tip. The fastener 10 can therefore be used to form the bore into which it is intended to be fastened without the need for a separate awling tool.

The gaps 26 separate adjacent body portions 16. The gaps 26 may have a non-uniform width along at least a portion of the length of the body 12. In this example, the width of the gaps 26 generally tapers in a direction towards the first end 22 of the body 12. The non-uniform width of the gaps 26, in particular the tapering of the gaps 26 towards the first end 22, facilitates the body portions 16 moving outwardly when they are intended to expand, while preventing the body portions 16 moving outwardly when the fastener 10 is used for awling.

FIGS. 2 to 6 show the shape of the body portions 16 in greater detail. It can be seen from the sequence of drawings of FIG. 2 to FIG. 6, which show various cross-sectional views along the length of the body portions 16, that the body portions 16 have non-uniform axial profiles along at least a portion of their respective lengths. In this example, the body portions 16 have a substantially trapezoidal cross section at a second end 26 of the body 16. The cross-sectional shape of each body portion 16 then transitions to a substantially triangular cross-sectional shape along the length of the body portion 16. The non-uniform cross section of the body portions 16 provides the general shape that can be seen in the body portion 16' shown in the partial cut away view of FIG. 6.

Figure 2:
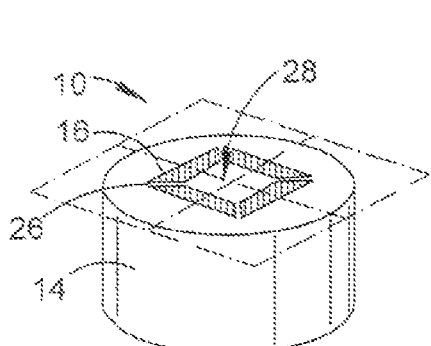
Figure 3:
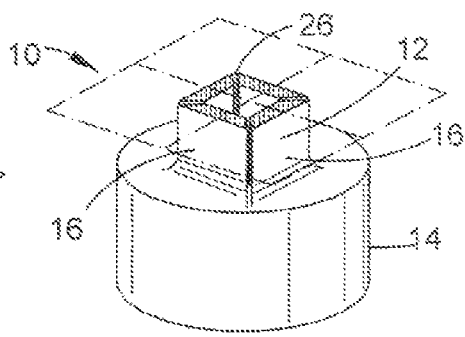
Figure 4:
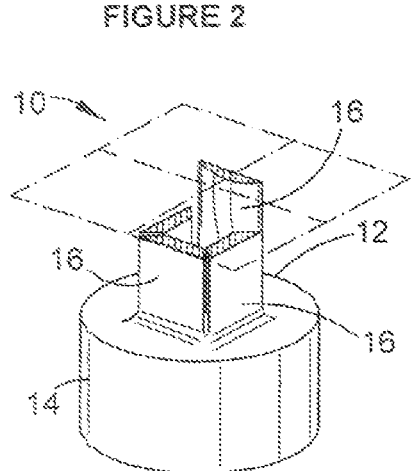
Figure 5:
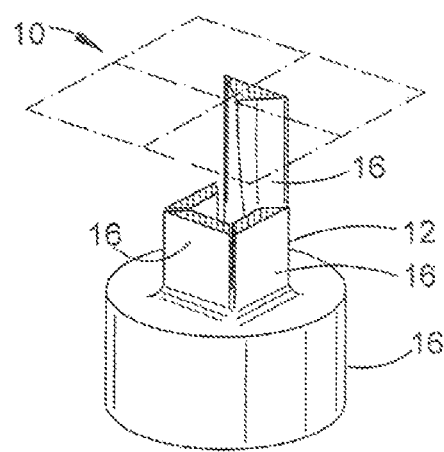

It can also be seen, for example by comparing FIG. 2 and FIG. 3, that the cross section of each body portion 16 becomes thinner before transitioning to the substantially triangular cross section. An example of a thin cross section 50 (see FIG. 6) is shown in more detail in FIGS. 7 and 8.

The fastener 10 is arranged to move from the contracted configuration to the expanded configuration when an actuating member (not shown) is inserted through an internal region 28 of the body 12, for example via an aperture (not shown) in the head 14. The actuating member will come into contact with a respective inner surface 30 of each body portion 16, for example a protrusion 32, which will urge each body portion 16 outwards, thereby moving the fastener 10 into the expanded configuration. The actuating member may be suitable a pin or screw or the like.

Providing the thin cross section 50 facilitates bending occurring at the corresponding region of the body portions 16 in preference to other regions of the body portions 16 when the fastener 10 moves from the contracted configuration to the expanded configuration. The position of the thin cross section 50 therefore provides control over where the bending should occur.

The cross section 50 is also shaped so as to minimise bending modulus and to allow for maximum expansion of the fastener 10 without plastic deformation. In this example, the functions of minimising bending modulus and allowing for maximum expansion are achieved by providing parallel inner and outer edges 62, 64. Further, the cross section 50 is shaped so as to reduce stress concentration, in this example by providing rounded corners 66 as shown in FIG. 8.

The fastener 10 has been described as comprising four body portions 16. This provides a substantially square profile that can increase rotational stability of the fastener 10 when its respective bore hole. It will be appreciated that the fastener 10 may comprise any appropriate number of body portions 16, such as three body portions 16 arranged to provide a substantially triangular profile.

Figure 9:
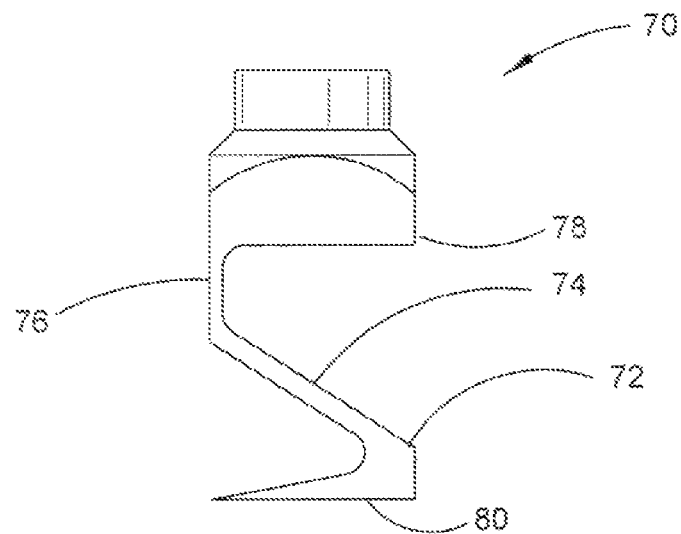
FIG. 9 shows a side view of a fastener in accordance with a further embodiment of the present invention.

Further variations of the fastener 10 are envisaged. For example, FIG. 9 shows a fastener 70 that is arranged to expand asymmetrically, in this example by expanding in only one direction. Instead of the four expanding body portions 16 of fastener 10, only one body portion 72 is provided. As there is only one body portion, the body portion 72 can be shaped such that a actuating surface 74, with which an actuating member can interact so as to urge the body portion 72 outwardly, extends substantially from a first side 76 of the fastener 70 to an opposite second side 78 of the fastener 70. An engaging portion 80 that is arranged to engage with the material into which the fastener 70 is to be fastened extends substantially from a lower end of the body portion 70 at the second side 78 to the first side 76. Such an arrangement allows the fastener 70 to expand further from a longitudinal axis of the fastener 70 compared to if the fastener 70 was provided with more than one body portion 72.

Figure 10:
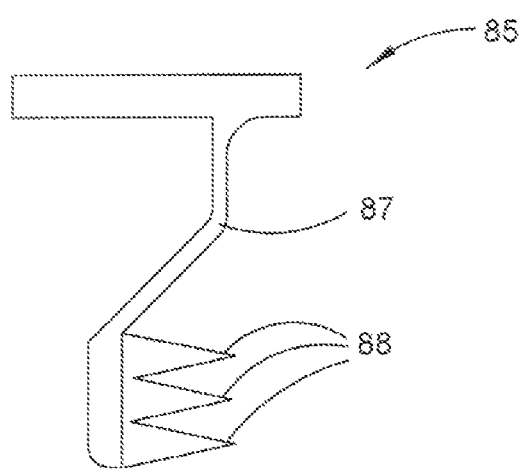
FIG. 10 shows a side view of a fastener in accordance with a further embodiment of the present invention.

In another alternative fastener 85 shown in FIG. 10, a body portion 87 may be provided with one or more spikes 88. Providing spikes 88 facilitates retaining the body portion 87 within material (such as bone) into which it is inserted by piercing rather than friction. Providing spikes 88 can facilitate reducing an amount of force required to engage the fastener 85 with the material into which it is inserted compared to if the spikes 88 were not provided.

Figure 11:
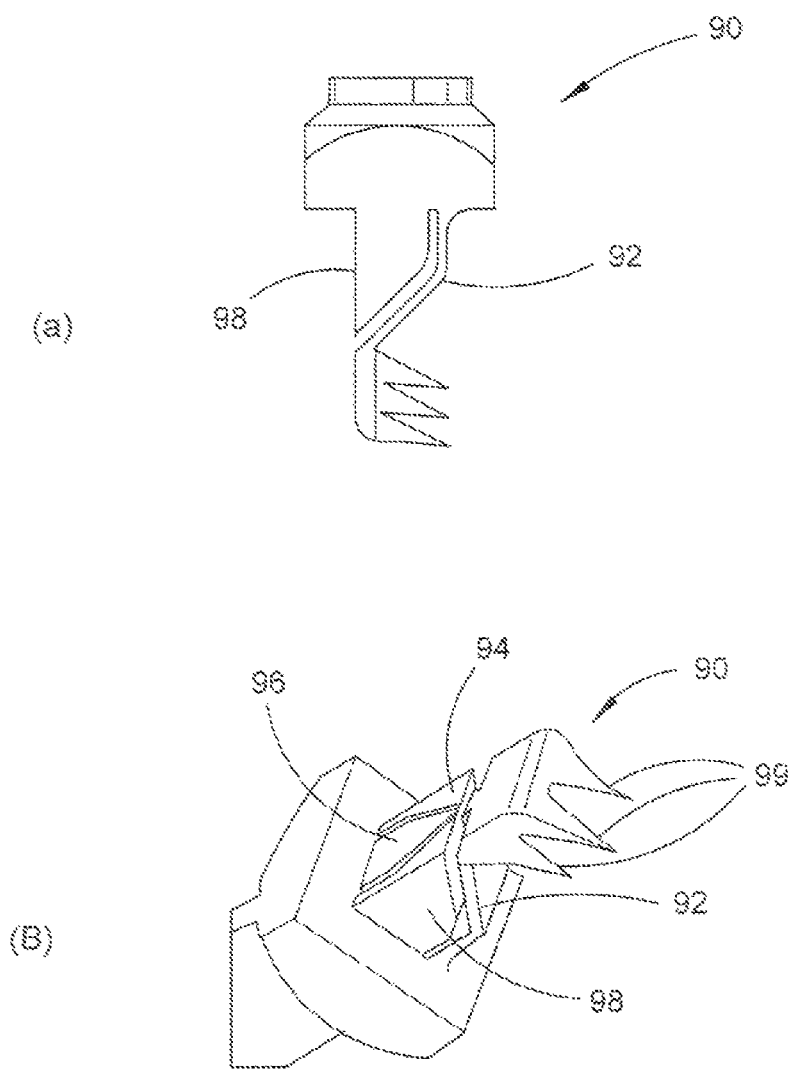
FIGS. 11 (a) and (b) show views of a fastener in accordance with a further embodiment of the present invention.

In a further alternative, fastener 90, shown in FIGS. 11 (*a*) and (*b*), comprises four body portions 92, 94, 96 and 98 that are arranged such that at least two body portions expand at different stages due to their different vertical configurations. For example, body portion 92, which is provided with spikes 99 in a similar arrangement to the fastener 85, will begin expanding after body portions 94, 96 and 98 have begun expanding as an actuating member will contact body portion 92 last. Such an arrangement can assist in increasing an expansion range of the fastener 90.

Figure 12:
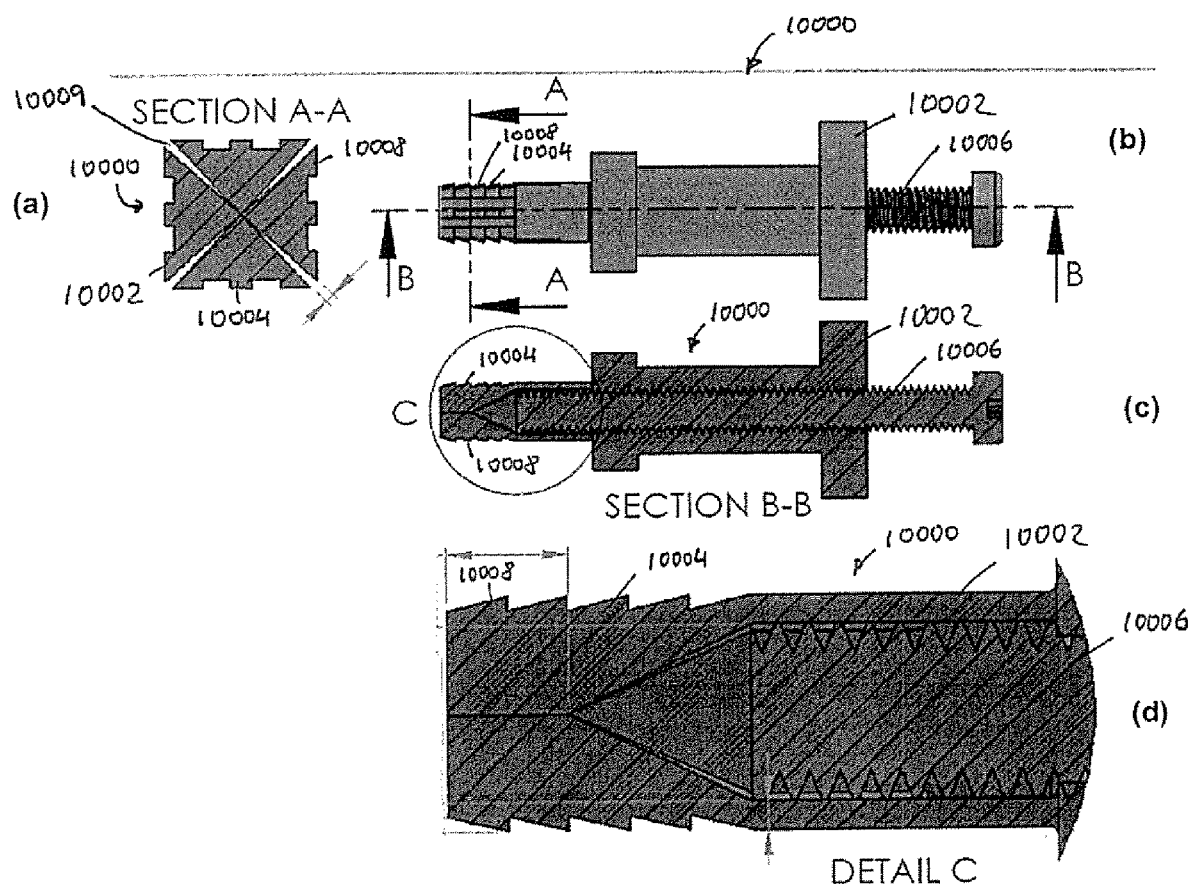
FIG. 12 (a) shows a side view and FIG. 12 (b) to (D) show cross-sectional views of a fastener in accordance with an embodiment of the present invention.
Figure 15F:
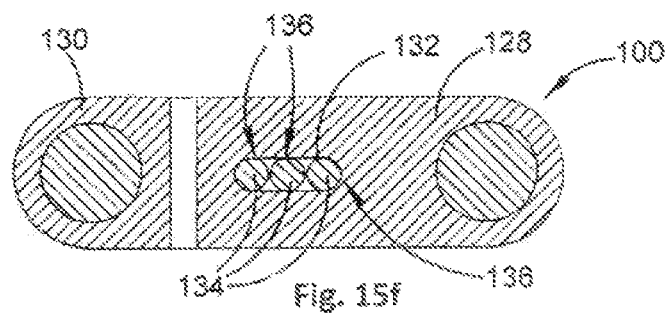
Figure 16A:
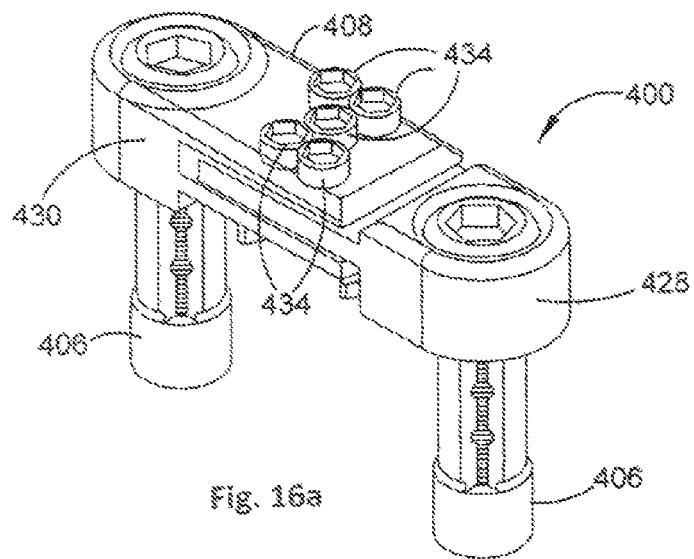
FIG. 16a is a perspective view of an orthopaedic stabilisation device in a contracted configuration in accordance with a further embodiment of the present invention.
Figure 16B:
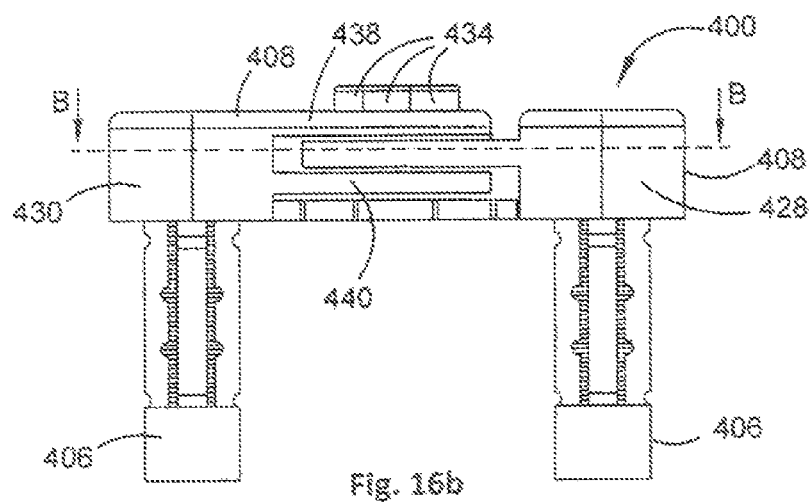

FIG. 12 (*a*) to (*d*) shows a fastener 10000, which relates to the fastener 10 described above with reference to FIG. 1. The fastener 10000 has a body 10002 from which four body portions 10004 project. Similar to the fastener 10, the fastener 10000 is arranged to move from a contracted configuration (as shown in FIG. 12) to an expanded configuration (not shown) when an actuating member is received. The actuating member is in this example provided in the form of a threaded bolt 10006. In the expanded configuration, the body portions 10004 of the body 10002 move outwardly, thereby facilitating fastening the fastener 10000 in a bore hole. In this embodiment the each body portion 10002 has a plurality of barbs 10008.

The body 10002 of the fastener 10000 has in this embodiment a length of 10 mm long, a width of 4 mm and expands to 7 mm using the threaded bolt 10006, which has a diameter of 3 mm.

The fastener 10000 was fabricated using a Selective Laser Sintering (SLS), a 3D printing process and was developed and manufactured especially for orthopaedic applications. The inventors hypothesise that known fasteners having a round cross-sectional shape have their expansion size limited by the high area moment of inertia of the expanded sections. In this embodiment the inventors address this by developing a fastener that has a substantially square cross-sectional shape, which allows the expanded sections in the design to be parallel, minimising expansion force and allowing maximum expansion before plastic yield of the expanded sections.

The expandable fastener 10000 is expanded by advancing the threaded bolt 10006 into a tapered hole of the fastener 10000. This allows the maximum expansion to occur at the bottom of the fastener 10000, maximizing the length of bone that was loaded during pull-out.

The theoretical expansion range of the fastener 10000, which the inventors hypothesized to be the main determinant of pull-out strength, is dictated by the width of the expansion walls and the diameter of the threaded bolt 10006. To maximize expansion the diameter of the threaded bolt 10006 was chosen to be 3 mm, which left 0.5 mm thickness for the expanded sections. With this configuration, the fastener 10000 theoretically expanded 2 mm in all four directions from 4 mm width to 8 mm width.

Using SLM, the slots 10009 in the fastener were made using a sacrificial perforation. The slots 10009 were designed to vary from 250 microns width at the edge to zero thickness at the centre (see section A-A shown in FIG. 12 (*a*)). This eliminates unnecessary slot width and maximizes expansion size.

The performance of the fastener 10000 was compared with that of conventional orthopaedic screws of 4 mm thread diameter as follows.

Thoracic spines were opportunistically harvested from 2 sheep cadavers. The spines were frozen at −20 degrees Celsius after extraction and thawed for 5 hours. The vertebrae were separated and the vertebral bodies were excised by cutting through the pedicles. The samples were again stored at −20 degrees Celsius and were then thawed for 5 hours, CT scanned and refrozen. The samples were then again thawed for 5 hours and subsequently a 4 mm square hole was awled for receiving the expandable fasteners 10000 using a specially designed square awl. Further, a hole having a diameter of 2.5 mm was drilled into the bone for receiving the conventional orthopaedic screws. The vertebrae were then rescanned after insertion of the fastener 10000 and the orthopaedic screw to determine their location in the bone. The samples were also scanned after being mechanically tested to failure to analyses the failure mode.

The samples were tested using the Instron 8874 servo-hydraulic materials testing machine. Before testing, the bone was thawed for 5 hours. The fasteners 10000 and orthopaedic screws were then implanted. PMMA bone cement (Vertex cold-curing acrylic denture repair material) was placed on the upper surface of the bone. Samples were then mounted in a custom rig that consisted of an upper section with a slot to restrain the fastener and a lower section with a plate with a 13 mm wide slot to restrain the upper section of the bone during pull-out. The Instron testing machine was manually moved until the bone cement compressed onto the plate forming a flat contact plane to ensure purely axial loading. Care was taken to ensure that excess bone cement inside the 13 mm slot was removed.

The fasteners 10000 had significantly higher yield load ($p=8.73E-7$) and ultimate load ($p=8.18E-7$) compared with the conventional orthopaedic screws. The variance in the fasteners 10000 was significantly lower than that for the screws for both failure load ($p=9.58E-8$) and maximum load ($p=1.81E-8$) indicating that, as there is no significant difference between the bone sample variance ($p=0.352$), the fasteners 10000 are less dependent of bone density. The fasteners 10000 had on average a 41% higher failure load and 43% maximum load than the screws. The failure energy was more than 3 times larger for the expandable fasteners.

It will be appreciated that each of the fasteners 10, 85, 90 and 10000 may be a component in an orthopaedic stabilisation device, such as the below-described orthopaedic stabilisation device 100 or variants thereof, and that each of the fasteners 10, 85, 90 and 10000 may share any appropriate features described in respect of the legs of the above-orthopaedic stabilisation device 100 or variants thereof.

Further it will be appreciated that an advantage provided by the above-described fastener is that its arrangement allows it to elastically deform when expanding, not least due to its substantially square cross-sectional profile. This can facilitate: reversing the expansion of the fastener which can allow the fastener to be removed; increasing fatigue performance of the fastener; and reducing the force required to expand the fastener, thereby allowing a greater range of expansion before the expansion force is large enough to damage the fastener.

In the following an orthopaedic stabilisation devices is described. The orthopaedic stabilisation device includes the above-described fastener. For example, the orthopaedic stabilisation device may be for facilitating the stabilisation of two or more bones or bone portions with respect to one another, and to fasteners that may be included in the orthopaedic stabilisation device for fastening the device to the bone, or that may be used in other fastening scenarios wherein fastening is required, such as masonry work.

The orthopaedic stabilisation device comprises at least two legs that are received in bore holes of respective bones, such as adjacent vertebrae, and a stabilisation member that bridges the two legs and facilitates stabilising the respective bones with respect to one another.

Each leg can be arranged to receive an element that results in fastening of the leg in its respective bore hole. The element that results in fastening of the leg in its respective bore hole may be a fastening element, such as a fastening screw, or may cause the leg to function as a fastening element, such as by causing the leg to expand and fasten in its respective bore hole.

The stiffness of the stabilisation member can be controlled, and a motion limit of the stabilisation member can be set, so as to provide dynamic stabilisation of the bones to which the orthopaedic stabilisation device is implanted. Such an orthopaedic stabilisation device can be used, for example, to stabilise two adjacent vertebrae whilst maintaining partial and controlled intervertebral motion.

The stabilisation member may also be static, which can prevent painful motion by restricting motion through fusion in conjunction with a graft.

The legs and the stabilisation member are arranged so as to facilitate insertion of the orthopaedic device into the bore holes in one piece. In this example, such an arrangement is achieved by integrating the legs and the stabilisation member. Such an arrangement obviates the need to align and adjust conventional orthopaedic fasteners and to couple the conventional orthopaedic fasteners to fusion instrumentation such as rods and plates that are used in conventional orthopaedic stabilisation devices.

The orthopaedic stabilisation device may be formed from titanium, or a material that promotes binding of the bone to the orthopaedic stabilisation device. The orthopaedic stabilisation device may also be formed from stainless steel, Delrin, polyetheretherketone or any other biocompatible material.

External surfaces of the orthopaedic stabilisation device may be relatively rough to facilitate the orthopaedic stabilisation device in engaging with the bone and to allow space for the bone to grow into the orthopaedic stabilisation device to facilitate effective osseointegration.

Referring now to FIG. 13, example orthopaedic stabilisation devices 100 are shown in use stabilising first and second adjacent vertebrae 102, 104. In this example, the first and second adjacent vertebrae 102, 104 are cervical vertebrae corresponding to the C6 and C7 cervical vertebrae respectively.

The orthopaedic stabilisation devices 100 are implanted into respective lateral masses of the first and second vertebrae 102, 104, with one orthopaedic stabilisation device 100 on each lateral side.

Each orthopaedic stabilisation device 100 comprises two legs 106 and a stabilisation member 108. Each leg 106 is implanted into a respective vertebra 102, 104, and the stabilisation member 108 functions to stabilise the vertebrae 102, 104 with respect to one another.

In this embodiment, the legs 106 and the stabilisation member 108 are arranged to be insertable into the bore holes in one piece. This is achieved by integrating the legs 106 and the stabilisation member 108.

FIGS. 14a and 14b show an example embodiment of the stabilisation device 100 in more detail. Each leg 106 is moveable from a contracted configuration, as shown in FIG. 14a, to an expanded configuration, as shown in FIG. 14b. When in the contracted configuration, the legs 106 are receivable within a respective bore hole in bone. The legs 106 are moveable to the expanded configuration when located in the bore hole to facilitate fastening each leg 106 within its respective bore hole.

Referring also to FIGS. 15a to 15f, the legs 106 each comprise a passage 110 that is arranged to receive an actuating member 112. The actuating members 112 are, in this example, threaded screws that are arranged, when rotated in a first direction, to urge the legs 106 towards the stabilisation member 108, thereby causing the legs 106 to move from the contracted configuration of FIG. 14a to the expanded configuration of FIG. 14b.

To facilitate this action, each actuating member 112 comprises a head portion 114 arranged to receive a hex-head screw driver or other tools for imparting rotation to the actuating member 112, and a threaded body portion 116. An internal surface 118 of a lower end of each leg 106 is threaded so as to engage with the threaded body portion 116.

As each leg 106 is urged towards the stabilisation member 108, the leg 106 will buckle at predefined locations. The buckling is facilitated by notches 120 arranged at predefined locations along an internal surface 122 of each of a plurality of leg struts 124 of each leg 106.

In this example, rotating the actuating member 112 in an opposite direction to the first direction will urge each leg 106 to move from the expanded configuration of FIG. 14b to the contracted configuration of 14a. This can facilitate removal of the orthopaedic stabilisation device 100 if desired, and provides an orthopaedic stabilisation device 100 that is moveable between the contracted and expanded configurations.

Moving each leg 106 to the expanded configuration increases a radial dimension of the leg 106 compared to when the leg 106 is in the contracted configuration, and facilitates retaining the leg within its respective bore hole. In this example, when the leg 106 moves to the expanded configuration, a middle portion 126 of each leg strut 124 is arranged to have an external surface that is substantially parallel to an axis of each leg 106, thereby increasing a surface area of each leg 106 that is in contact with bone. Such an arrangement can increase a pull-out strength of the orthopaedic stabilisation device 100.

The stabilisation member 108 is arranged such that a length of the stabilisation member 108 is alterable. In this example, the stabilisation member 108 comprises a first stabilisation portion 128 and a second stabilisation portion 130, wherein the first and second stabilisation portions 128, 130 can move relative to one another.

An amount by which the stabilisation portions 128, 130 can move relative to one another is constrained by a predefined amount, and hence an amount by which the length of the stabilisation member 108 can be altered is constrained. Constraining the relative motion of the first and second stabilisation portions 128, 130 is achieved in this example by providing an elongate slot 132 (see FIG. 15f) in the first stabilisation member that can engage with one or more pins 134 that can be inserted through, or removed from, respective apertures 136 provided in the second stabilisation portion 130.

Inserting a pin 134 into, or removing a pin from, different apertures 136 will provide different ranges of motion. It will also be appreciated that the first and second stabilisation portions 128, 130 can be prevented from moving relative to one another by inserting a pin 134 into each aperture 136, or at least into the apertures 136 that correspond with ends of the elongate slot 132.

In this example, the second stabilisation portion 130 comprises an upper plate 138 and a lower plate 140, the elongate slot 132 of the first stabilisation portion 128 being received therebetween. The upper and lower plates 138, 140 each comprise the apertures 136 for receiving the pins 134, thereby increasing a stability of the orthopaedic stabilisation device 100. However, to simplify manufacturing the device may be constructed using only one plate with an aperture and one slotted plate.

It will be appreciated that other slot and pin configurations can be used to provide different motion constraint options to the orthopaedic stabilisation device. For example, and as shown in FIGS. 16a to 16d, there is shown an orthopaedic stabilisation device 400 having an alternative slot and pin configuration to that of orthopaedic stabilisation device 100. The orthopaedic device 400 is similar to the orthopaedic device 100, and comprises two legs 406 and a stabilisation member 408. The stabilisation member 408 comprises a first stabilisation portion 428 and a second stabilisation portion 430, the first and second stabilisation portions 428, 430 being moveable relative to one another.

In this example, the first stabilisation portion 428 comprises three elongate slots 432 (see FIG. 16d) that are arranged to receive pins 434, and the second stabilisation portion 430 comprises a plurality of apertures 436 that are arranged to receive or reject the pins 434. With this arrangement, pins 434 can be placed as desired to constrain both linear and rotational motion of the first and second stabilisation portions 428, 430 with respect to one another. As with the orthopaedic stabilisation device 100, the second stabilisation portion 430 comprises upper and lower plates 438, 440 so as to increase a stability of the orthopaedic stabilisation device 400. However, to simplify manufacturing the device may be constructed using only one plate with an aperture and one slotted plate. Furthermore any number of elongate slots 432 can be used to strike a balance between simplifying manufacturing and providing more choice in range of motion.

Referring back to FIGS. 15a to 15f, the orthopaedic stabilisation device 100 also comprises a live spring 142 that couples the first and second stabilisation portions 128, 130 to one another in addition to the coupling between the elongate slot 132 and the pin(s) 134. The live spring 142 facilitates control of a stiffness of the stabilisation member 108, and can assist in reducing impulse loading of the legs 106 and preventing confounding relative motion of the legs 106 during implantation. Further, when the orthopaedic stabilisation device 100 is used to stabilise vertebrae, the live spring 142 can assist in reducing motion and loading of facet joints of the vertebrae during small movements of the spine to minimise incidence or severity of facet arthritis. If a stiffness control mechanism, such as the live spring 142, is not provided, then impulse loading of the legs 106 caused by free movement of the stabilisation member 108 may lead to accelerated loosening of the legs 106 from their respective bore holes. Further, if the orthopaedic stabilisation device 100 can freely move throughout its predefined variable length during implantation, then aligning the legs 106 to their respective bore holes may present a challenge to a surgeon performing the implantation. Finally, in the case of facet arthritis, minimising movement and loading sharing at the facet joints during micro-motions of the vertebrae can facilitate treating, and preventing further, degeneration of the facet joints. However if these problems can be solved without using a spring then the orthopaedic stabilisation device 100 can be constructed without a spring also.

In this example, the live spring 142 is formed from an appropriate metal or metal alloy and the live spring 142 is bent in a zig-zag fashion in a plane that is parallel to section A-A.

The orthopaedic stabilisation devices 100, 400 represent just two example embodiments, and features of the orthopaedic stabilisation devices 100, 400 can be implemented in many different ways. Further example features of orthopaedic devices will now be described.

The legs 106, 406 of orthopaedic devices 100, 400 can be arranged to move from the contracted configuration to the expanded configuration, or between the contracted and expanded configurations, in many different ways to facilitate fastening the legs 106, 406 in their respective bore holes.

Referring to FIG. 17a, there is shown an example leg 506 that is arranged to move from a contracted configuration (FIG. 17a) to an expanded configuration (FIG. 17b) in a buckling action in response to movement of an actuating member 512 in a direction out of bone 502 that the leg 506 is inserted into.

The leg 506 comprises a plurality of notches 520 arranged on an internal surface of each leg strut 524, and a plurality of notches 520' arranged on an external surface of each leg strut 524. The notches 520, 520' facilitate each leg strut 524 buckling in a predetermined manner when the actuating member 512 moves out of the bone 502. In this example, the actuating member 512 comprises an end portion 550 that is arranged to engage with a remote end of the leg 506 and to urge the leg 506 into the expanded configuration shown in FIG. 17b.

Figures 18A, 18B:
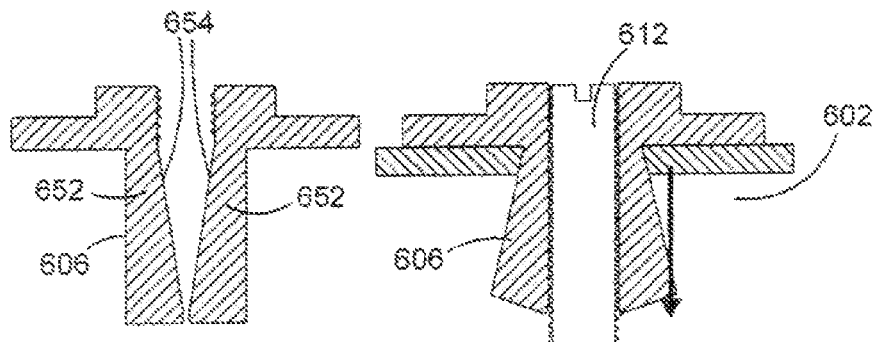
FIG. 18a is a cross-sectional view of a leg of an orthopaedic stabilisation device in a contracted configuration in accordance with an embodiment of the present invention.
FIG. 18b is a cross-sectional view of the leg of FIG. 18a in an expanded configuration.

Referring to FIG. 18a, there is shown an example leg 606 that is arranged to move from a contracted configuration (FIG. 18a) to an expanded configuration (FIG. 18b) in a cantilever action in response to movement of an actuating member 612 in a direction into bone 602 that the leg 606 is inserted into.

The leg 606 comprises leg portions 652 having respective angled internal surfaces 654 that are arranged to be urged outwards when the actuating member 612 is moved in a direction into the bone 602, thereby moving the leg 606 into the expanded configuration as shown in FIG. 18b.

Figures 19A, 19B:
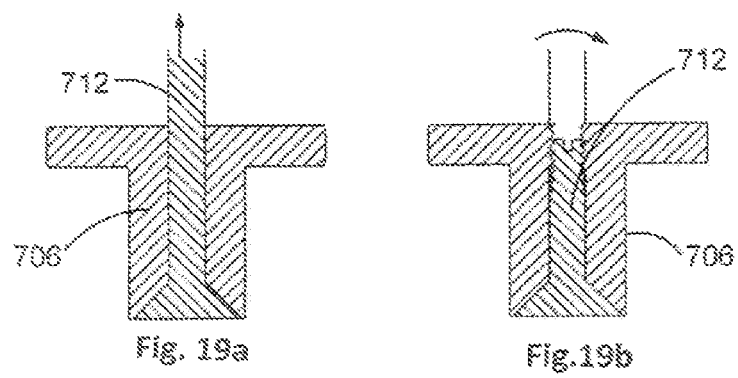
FIG. 19a is a cross-sectional view of a leg of an orthopaedic stabilisation device in accordance with an embodiment of the present invention.
FIG. 19b is a cross-sectional view of a leg of an orthopaedic stabilisation device in accordance with an embodiment of the present invention.

FIGS. 19a and 19b illustrate different methods of urging legs 706 from the contracted to the expanded configuration. In FIG. 19a, an actuating member 712 can be moved linearly, such as by an upwards pulling action or a downwards pressing action, to urge the leg 706 into the expanded configuration. In FIG. 19b, an actuating member 712 can be rotated to urge the leg 706 into the expanded configuration.

For embodiments wherein the actuating member 712 is moved linearly upwards to effect expansion of the leg 706, a portion of the actuating member 712 may be arranged to be removable. This can prevent the actuating member 712 from protruding from the orthopaedic stabilisation device 100. Example embodiments of such an arrangement are shown in FIGS. 20a to 20f.

Figures 20A, 20B, 20C, 20D, 20E, 20F:
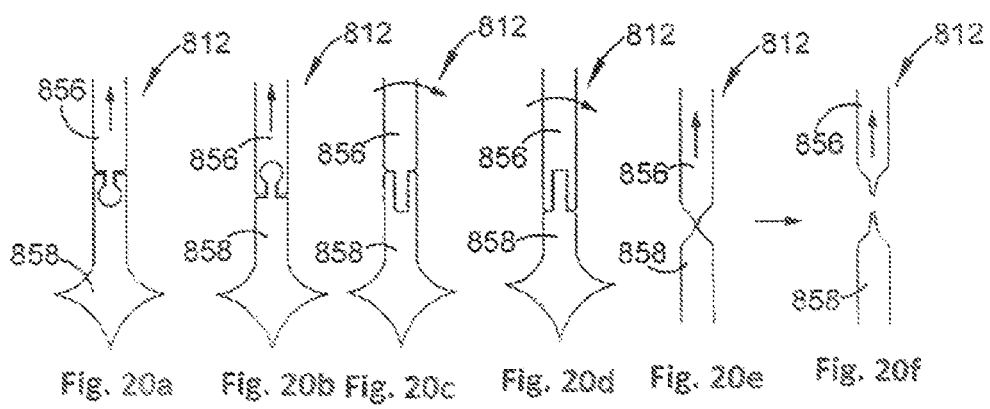
FIGS. 20a to 20f are cross-sectional views of actuating members of an orthopaedic stabilisation device in accordance with embodiments of the present invention.

An upper portion 856 of an actuating member 812 can be removed from a lower portion 858 of the actuating member 812 by a snap fit disconnection (FIGS. 20a and 8b), a threaded disconnection (FIGS. 20c and 20d) or a permanent rupture (FIGS. 20e and 20f).

Figure 21:
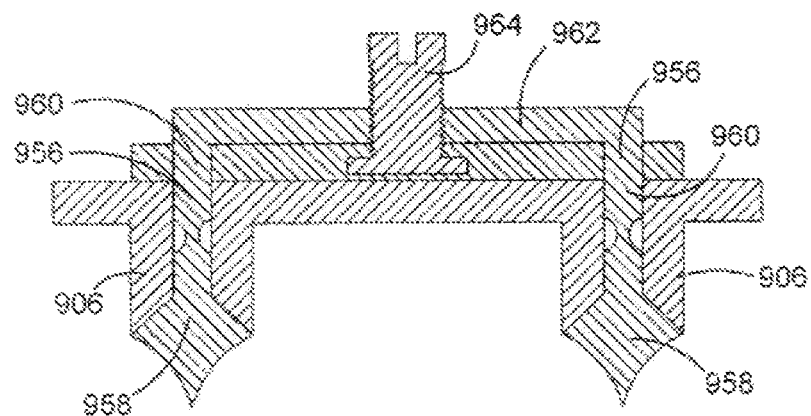
FIG. 21 is a cross-sectional view of an orthopaedic stabilisation device in accordance with an embodiment of the present invention.

It will be appreciated that the legs 106 of the orthopaedic stabilisation device 100 can be moved from the contracted to the expanded configuration simultaneously or separately. Separate expansion of each leg 106 can be achieved by separately moving respective actuating members 112, for example with a screw driver having an appropriate head profile or a specially designed tool. An example of an arrangement whereby simultaneous expansion of legs 906 can be effected is illustrated in FIG. 21.

In this example, an actuating member 912 is provided that comprises two leg portions 960 that are arranged to be received by respective legs 906, and that are coupled together by a bridge portion 962. Both leg portions 960 can be moved upwards in one action to expand the legs 906 simultaneously by pulling a handle portion 964 upwards either directly or through a threaded advancement caused by revolving a threaded member. In this example, each leg portion 960 comprises a lower portion 958 and an upper portion 956, the upper portion 956 being removable from the lower portion 958 in a similar manner to that as shown in FIGS. 20e and 20f.

Providing an arrangement whereby the legs 906 can be expanded simultaneously can assist in reducing surgical time when implanting the orthopaedic stabilisation device 100 and may reduce difficulty in lining up the orthopaedic stabilisation device 100 prior to expanding the legs 906.

Figure 22:
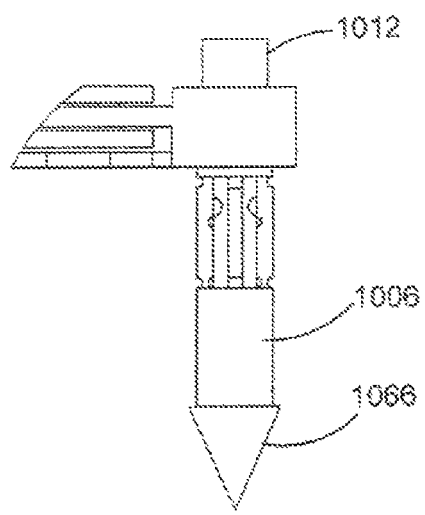
FIG. 22 is a side view of a leg of an orthopaedic stabilisation device in accordance with an embodiment of the present invention.

FIG. 22 shows an example leg 1006 that is arranged to receive an actuating member 1012 having an awling tip 1066. The awling tip 1066 can assist in implanting the orthopaedic stabilisation device 100, as the awling tip 1066 can be used to punch the bore hole in the bone to which the leg 1006 is to be fastened. It will be appreciated, however, that any suitable device can be used to create the bore hole, such as a separate awling tool or drill.

Figure 23:
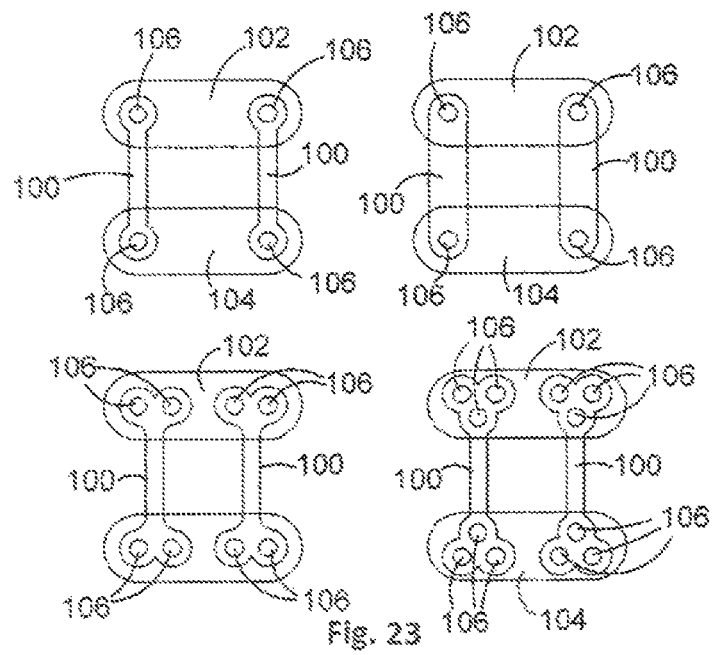
FIG. 23 is a schematic diagram of various orthopaedic stabilisation devices in use stabilising adjacent vertebrae in accordance with an embodiment of the present invention.

It will be appreciated that, although the above examples relate to an orthopaedic stabilisation device 100 having two legs 106, any number of legs 106 can be provided. For example, FIG. 23 shows a variety of top views of orthopaedic stabilisation devices 100 being used to stabilise first and second vertebrae 102, 104. The examples shown in FIG. 23 illustrate orthopaedic stabilisation devices 100 having two, four, and six legs 106.

Figure 24A:
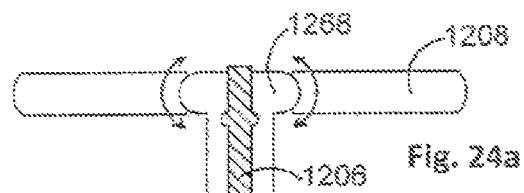
FIGS. 24a to 24c are cross-sectional views of a leg of an orthopaedic stabilisation device in accordance with an embodiment of the present invention.
Figure 24B:
Figure 24C:
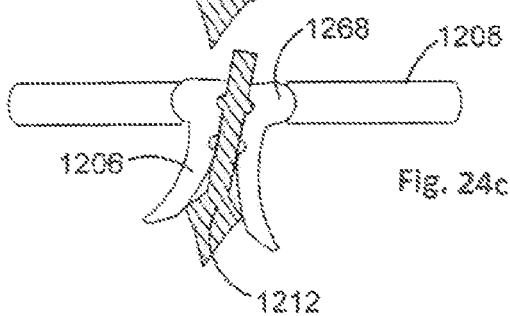

In some embodiments, an angle of each leg 106 with respect to a plane of the stabilisation member 108 can be arranged to be varied as desired. For example, and as shown in FIGS. 24a to 24c, an angle of a leg 1206 can be varied using a locking plate mechanism. The locking plate mechanism works by expanding a rotational portion 1268 of the leg 1206 to press fit into a plate to which the leg 1206 is coupled, such as a portion of the stabilisation member 1208. In this example, the rotational portion 1268 is expanded when an actuating member 1212 is moved upwards, for example when expanding the leg 1206. Expansion of the rotational portion 1268 causes friction or interference between the rotational portion 1268 and the stabilisation member 1208 to which the rotational portion 1268 is coupled, locking the orientation of the leg 1206.

Each leg 106 may comprise a plurality of barbs. An example leg 1306 comprising a plurality of barbs 1370 is shown in FIG. 25a. The barbs 1370 can increase friction between the leg 1306 and bone into which the leg 1306 is implanted, and are elastically retracted during implantation. The barbs 1370 may be any appropriate shape, examples of which are shown in FIG. 25b. Blunt barbs 1370, such as barbs 1370 having an elliptical profile, may assist in preventing stress concentration, crack initiation and eventual fatigue failure.

The axial profile of each leg 106 and their respective actuating members 112 can be any appropriate shape, such as circular, triangular or square. Some axial profiles, such as a circular profile, may provide manufacturing benefits. Non-rotationally symmetric profiles, such as a square profile, may provide benefits when implanted in bone as they can facilitate preventing rotation. Example legs 1406 and actuating members 1412 having square profiles are shown in FIG. 26.

The action by which the legs 106 expand can be any appropriate action. The example orthopaedic stabilisation devices 100, 400 described earlier are arranged to expand by a buckling action in response to the actuating member 112 moving in a direction out of the bone. In the examples, the legs 106 comprise four leg struts 124 that have notches 120 to facilitate buckling of the leg struts 124 at the locations of the notches 120. It will be appreciated that any number of leg struts 124 and/or notches 120 can be provided. Providing a plurality of notches 120 on a leg strut 124 can provide a leg 106 that has multiple stages of expansion.

It will be appreciated that other arrangements for achieving expansion of the legs 106 are envisaged. An alternative arrangement is illustrated in FIG. 27. In this example, a leg 1506 comprises a plurality of washers 1572, each washer having a notch 1574 to facilitate buckling of the washer 1572. The washers 1572 are separable, and can be coupled together by respectively threaded end portions, thereby providing a leg 1506 that has a length that can be set as desired.

As described earlier, the legs 106 can be arranged so as to be moveable between the contracted and expanded configurations. An example of a mechanism for facilitating this type of arrangement is shown in FIG. 28. In this example, a lower portion 1676 of an actuating member 1612 is arranged to be received by a correspondingly shaped region of a leg 1606 such that the actuating member 1612 can be moved upwards and downwards to effect moving the leg 1606 between the contracted and expanded configurations.

Figure 29:
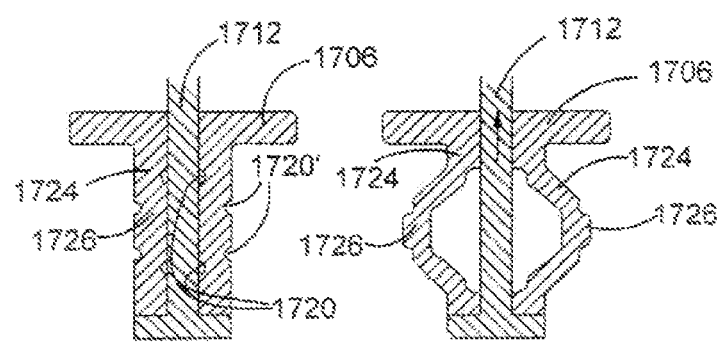
FIG. 29 is a cross-sectional view of a leg of an orthopaedic stabilisation device in accordance with an embodiment of the present invention, the leg being shown moving from a contracted to an expanded configuration.

Further, and as described earlier, each leg 106 may be arranged such that, when expanded, a middle portion 126 of each leg strut 124 is arranged to have an external surface that is substantially parallel to an axis of each leg 106, thereby increasing a surface area of each leg 106 that is in contact with bone. An example of such an arrangement is illustrated in FIG. 29. In this example, internal notches 1720 and external notches 1720' of each leg strut 1724 are arranged such that a middle portion 1726 of each leg strut is substantially parallel to an axis of each leg 1706 when the actuating member 1712 is moved upwards and the leg 1706 moves to the expanded configuration.

Figure 30:
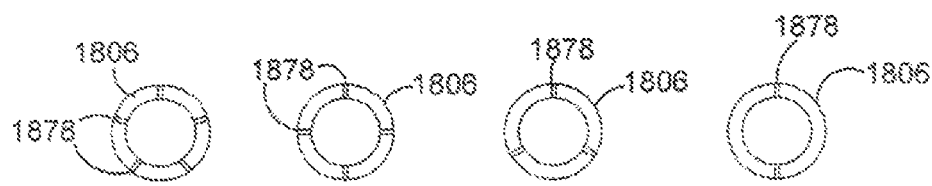
FIG. 30 shows various end views of legs of an orthopaedic stabilisation device in accordance with an embodiment of the present invention.
Figure 31:
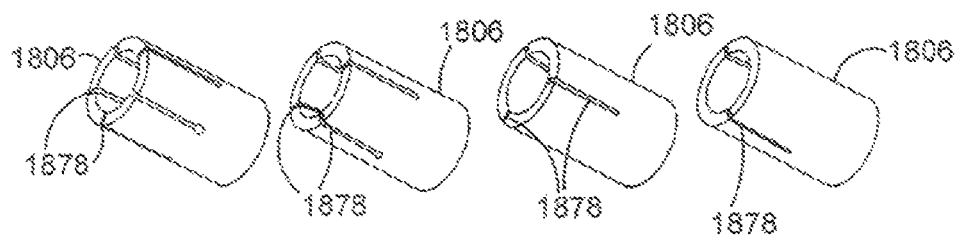
FIG. 31 shows partial perspective views of the legs of FIG. 30.

As described earlier, the legs 106 may be arranged to expand in a cantilever action. FIGS. 30 and 31 illustrate example configurations of portions of a leg 1806 that can facilitate cantilever deformation as the leg 1806 moves to the expanded configuration. The legs 1806 may comprise any number of longitudinal slots 1878. Increasing the number of longitudinal slots 1878 will reduce the force needed to expand the legs 1806.

Figure 32:
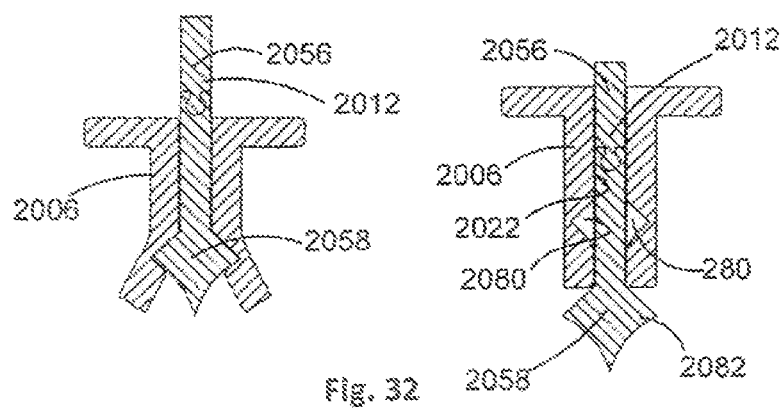
FIG. 32 is a cross-sectional view of a leg of an orthopaedic stabilisation device in accordance with an embodiment of the present invention, the leg being shown in a contracted and an expanded configuration.

With arrangements wherein the legs 106 are arranged to expand in a cantilever action, an internal surface 2022 of a leg 2006 can be provided with snap fit grooves 2080 that have a complementary shape to an outer portion 2082 of a head of the actuating member 2012. This is illustrated in FIG. 32. In this way, the outer portion 2082 can be retained in the grooves 2080 when the actuating member 2012 is moved upwards and the leg 2006 is moved to the expanded configuration, thereby preventing the actuating member 2012 from backing out of the leg 2006 and moving the leg 2006 back to the contracted configuration, or a partially contracted configuration. Furthermore the snapping sound of the internal surfaces impacting the snap fit grooves will give confidence to the surgeon that the fastener has been sufficiently fastened, preventing over and under tightening of the device. In this example, the actuating member 2012 comprises separable upper and lower portions 2056, 2058.

Figure 33:
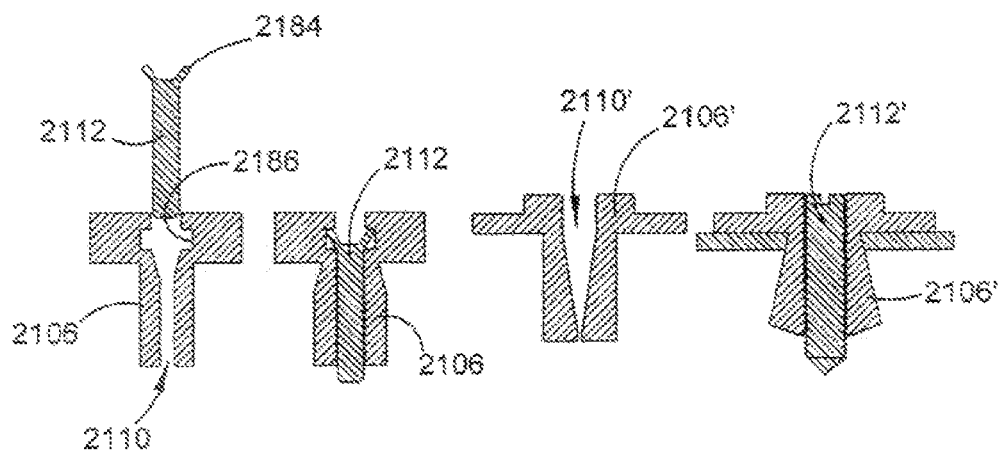
FIG. 33 shows cross-sectional views of various legs of an orthopaedic stabilisation device in accordance with embodiments of the present invention, the legs being shown in contracted and expanded configurations.

The legs 106 may be arranged to expand when the actuating member 112 is inserted into the passage 110 to provide a friction fit into bone. For example, and as shown in FIG. 33, a leg 2106 may comprise a passage 2110 that decreases in diameter along a length of the leg 2106, or a passage that has a constant diameter along the length of the leg 2106 that is smaller than that of the actuating member 2112. An actuating member 2112 can be inserted into the passage 2110, thereby causing the leg 2106 to expand so as to form an interference fit with the surrounding bone. An upper portion 2184 of the actuating member 2112 may protrude outwards and can be retained in a correspondingly shaped groove 2186 of the leg 2106 when the actuating member 2112 has been inserted into the leg 2106 and the leg 2106 has moved to the expanded configuration, thereby preventing the actuating member 2112 from backing out of the leg 2106 and moving back to the contracted configuration, or a partially contracted configuration.

A threaded actuating member 2112' can be provided, and a passage 2110' of a leg 2106' can be arranged to expand when the actuating member 2112' is inserted into the passage 2110'. An internal surface of the passage 2110' can be threaded to facilitate insertion of the actuating member 2112'. Alternatively, the internal surface of the passage 2110' can be unthreaded and formed from a softer material than the actuating member 2112', wherein the actuating member 2112' threads into the internal surface of the passage 2110' when inserted into the passage 2110'. Alternatively the actuating member 2112' can be non-threaded and the expansion action can comprise a linear impact, such as from a hammer or a linear pull such as for a pot-rivet.

In both cases, an external surface of the legs 2106, 2106' can be roughened, and/or may be provided with barbs, ridges, or spikes to facilitate the interference fit with the surrounding bone.

Figure 34:
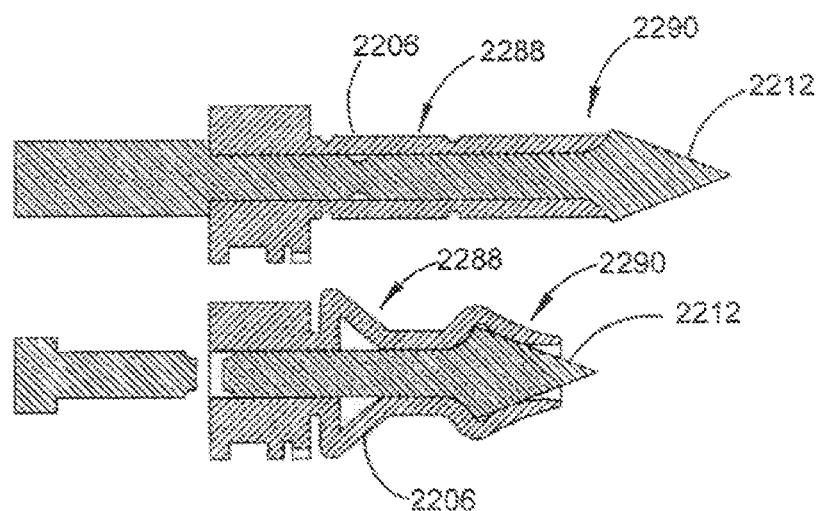
FIG. 34 is a cross-sectional view of a leg of an orthopaedic stabilisation device in accordance with an embodiment of the present invention, the leg being shown in a contracted and an expanded configuration.

The legs 106 may be arranged to use a combination of various expanding actions. For example, and as shown in FIG. 34, a leg 2206 may comprise a first portion 2288 that is arranged to move to the expanded configuration in a buckling action in response to movement of the actuating member 2212, similar to the buckling action described above, and a second portion 2290 that is arranged to move to the expanded configuration in a cantilever action, similar to the cantilever action described with reference to FIG. 18. The first portion 2288 can provide effective clamping of the leg 2206 to a cortical bone of a vertebra, and the second portion 2290 can prevent wastage of a lower region of the leg 2206 and increase a fixation with cancellous bone of a vertebra.

Referring back to FIGS. 14a, 14b and 15a to 15f, the stabilisation member 108 will now be described in more detail.

Figures 35A, 35B:
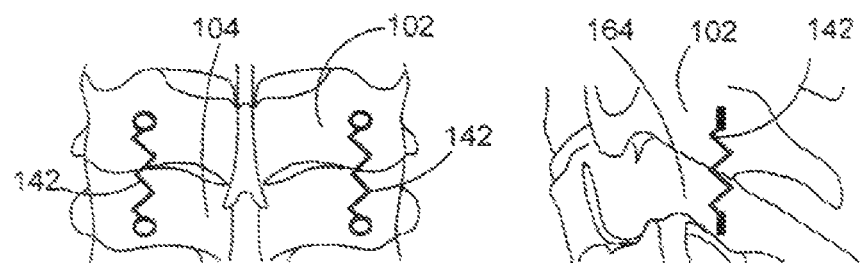

The live spring 142 of the stabilisation member 108 can be bent in the coronal plane and/or the sagittal plane, as shown in FIGS. 35a and 35b. The live spring 142 can also have no bends, or it may have one or more bends. The profile of the bends may be any appropriate shape, such as square, circular or triangular. A continuous profile, such as a circular profile, may reduce stress concentration, increasing fatigue life. In contrast, square bends are inherently less stiff and can provide more extension and compression for a given active length.

A cross-sectional profile of the live spring 142 may be any appropriate shape, such as elliptical, rectangular, square, circular or triangular.

Although a single live spring 142 is provided in this example, it will be appreciated that any number of springs or flexible members can be used. An increased number of springs can increase a stability and stiffness of the stabilisation member 108.

Figures 36A, 36B, 36C:
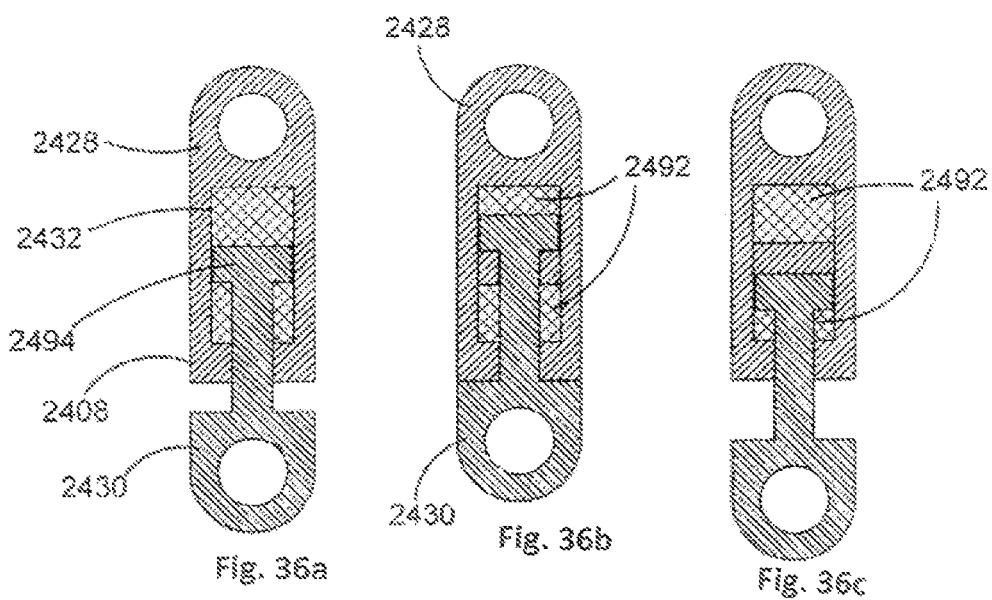
FIGS. 36a to 36c are top views of a stabilisation member of an orthopaedic stabilisation device in accordance with an embodiment of the present invention, the stabilisation member being shown in various stages of compression or expansion.

Other mechanisms for controlling a stiffness of the stabilisation member 108 are envisaged. For example, and with reference to FIGS. 36a to 36c, the stiffness of a stabilisation member 2408 can be controlled by compressible elements 2492 that are arranged in a slot 2432 of a first stabilisation portion 2428 of the stabilisation member 2408. A plate member 2494 of a second stabilisation portion 2430 will interact with, and meet resistance from, the compressible elements 2492 as the second stabilisation portion 2430 moves towards the first stabilisation portion 2428 (FIG. 36b) or away from the first stabilisation portion 2428 (FIG. 36c) from a neutral position (FIG. 36a).

The compressible elements 2492 can be made from any suitable material, such as rubber, polymers, or any other elastic material. There may be any number of compressible elements 2492, and the compressible elements 2492 can be used in series or in parallel. The compressible elements 2492 can be integrated together to increase stability and/or to simplify manufacture of the compressible elements 2492. The compressible elements 2492 can be formed in any appropriate shape so as to modify the force required to deform the compressible elements 2492.

Figure 37:
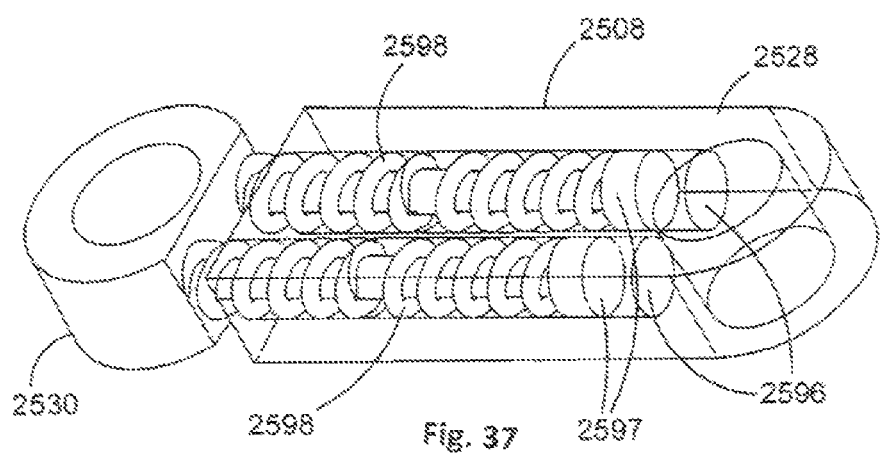
FIG. 37 is a partial cut away view of a stabilisation member of an orthopaedic stabilisation device in accordance with an embodiment of the present invention.

A stiffness of the stabilisation member 108 can also be controlled by using curved helical springs, as illustrated in FIG. 37. In this example, a first stabilisation portion 2528 of a stabilisation member 2508 comprises two passages 2596 for receiving respective legs 2597 of a second stabilisation portion 2530 of the stabilisation member 2508. A helical spring 2598 is coiled around each leg 2597 to provide stiffness control to the stabilisation member 2508. The helical springs 2598 can be any appropriate cross-sectional shape, such as elliptical, rectangular, square, circular or triangular. The helical springs 2598 can have any appropriate number of coils, wire thickness, coil diameter and can be formed from any appropriate material.

Figure 38A:
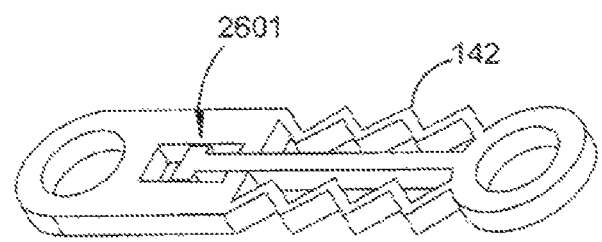
FIG. 38a is a perspective view of a stabilisation member of an orthopaedic stabilisation device in accordance with an embodiment of the present invention, the stabilisation member being arranged such that a stiffness mechanism is in series with a motion limit mechanism.
Figure 38B:
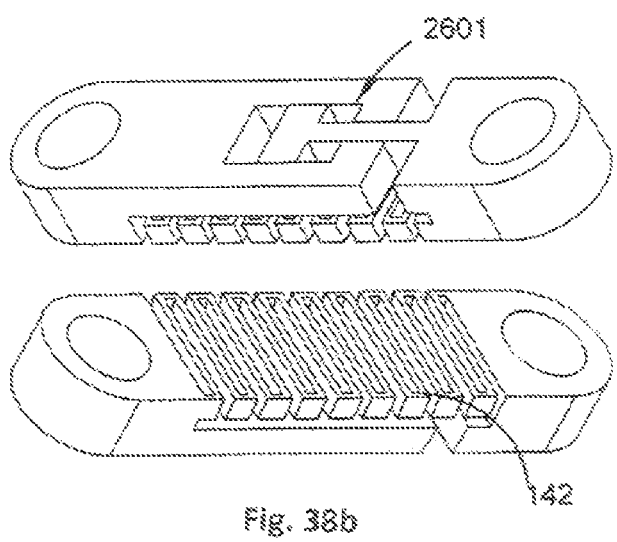
FIG. 38b shows top and bottom perspective views of a stabilisation member of an orthopaedic stabilisation device in accordance with an embodiment of the present invention, the stabilisation member being arranged such that a stiffness mechanism is in parallel with a motion limit mechanism.

As discussed earlier, the stabilisation member 108 also functions to define limits of motion of the orthopaedic stabilisation device 100. The stiffness control mechanism, such as that provided by the live spring 142, can be in series (see FIG. 38a) or in parallel (see FIG. 38b) with the mechanism that is used to define the limits of motion of the orthopaedic stabilisation device 100. In the examples of FIGS. 38a and 38b, a motion limit control mechanism 2601 is provided by a 'plate-in-plate' configuration as described later with reference to FIG. 43.

It will be appreciated that the motion limit control function could be provided by the stiffness control mechanism, such as by the live spring 142 and so a separate mechanism to define the limits of motion is not essential.

Figure 39:
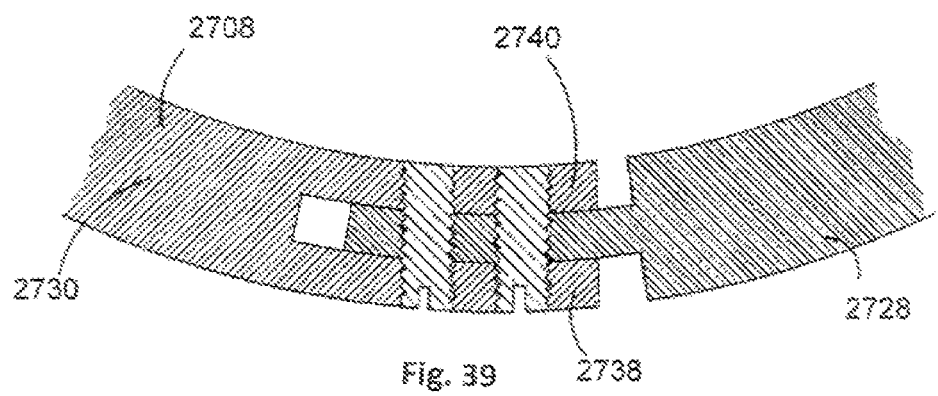
FIG. 39 is a partial cross-sectional view of a stabilisation member of an orthopaedic stabilisation device in accordance with an embodiment of the present invention.
Figure 40:
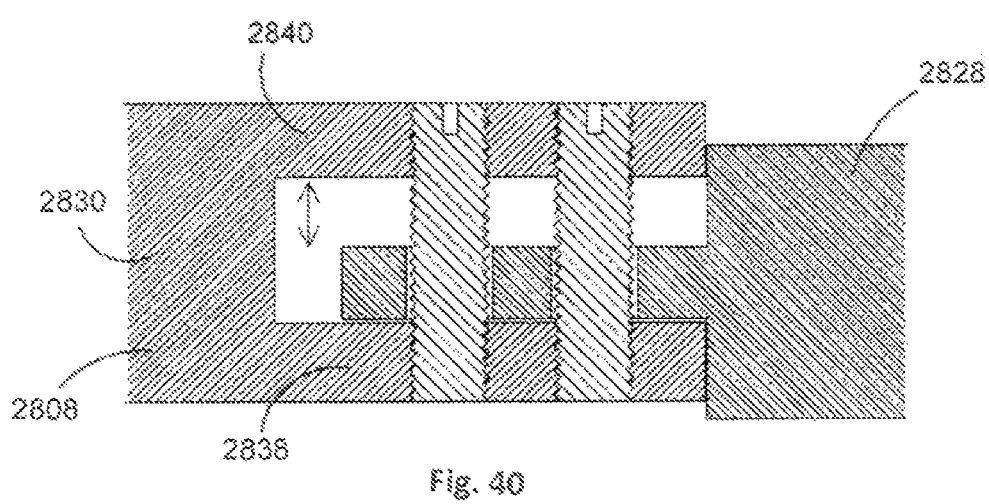
FIG. 40 is a partial cross-sectional view of a stabilisation member of an orthopaedic stabilisation device in accordance with an embodiment of the present invention.

The stabilisation member 108 may have a profile that more accurately imitates spinal motion compared to planar first and second stabilisation portions 128, 130. An example of such an arrangement is shown in FIG. 39, wherein first and second stabilisation portions 2728, 2730 of a stabilisation member 2708 are arcuate. Upper and lower plates 2738, 2740 of the second stabilisation portion 2730 are also arcuate.

Alternatively, if a truly physiological path of motion is not essential the stabilisation member 108 can also be arranged to facilitate at least some rotation of the first and second stabilisation portions 128, 130 relative to one another to approximate physiological movement. In one example, shown in FIG. 40, upper and lower plates 2838, 2840 of a second stabilisation portion 2830 or a stabilisation member 2808 are arranged such that there is clearance when a first stabilisation portion 2828 is received therebetween, thereby facilitating rotation of the first and second stabilisation portions 2828, 2830 with respect to one another.

Figure 41:
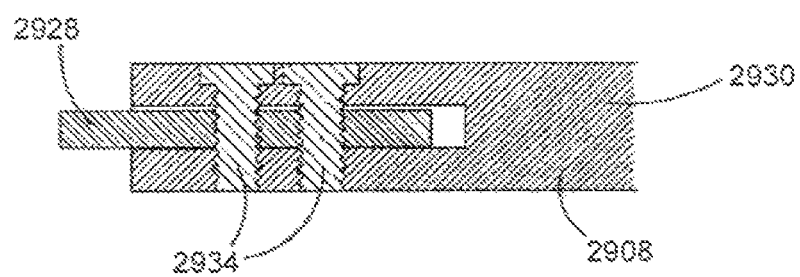
FIG. 41 is a partial cross-sectional view of a stabilisation member of an orthopaedic stabilisation device in accordance with an embodiment of the present invention.
Figure 42:
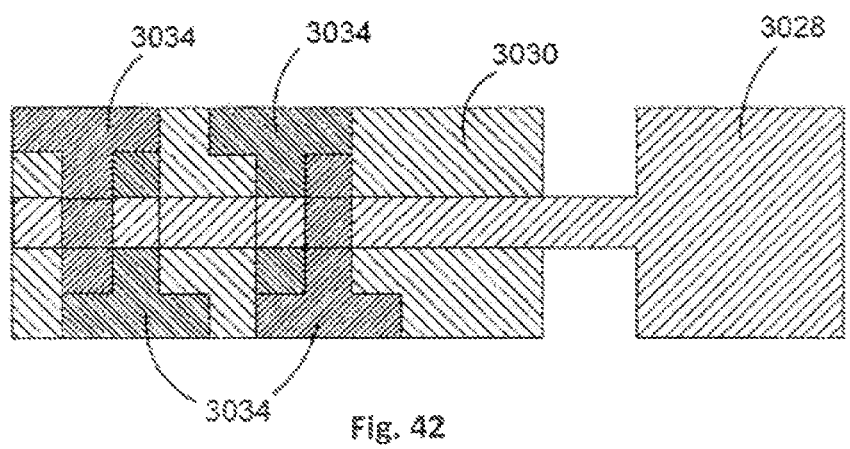
FIG. 42 is a partial cross-sectional view of a stabilisation member of an orthopaedic stabilisation device in accordance with an embodiment of the present invention.

In the example orthopaedic stabilisation devices 100, 400, the motion limits are defined by a slot and pin mechanism. As shown in FIG. 41, pins 2934 used to couple together first and second stabilisation portions 2928, 2930 of a stabilisation member 2908 may have a larger diameter at an end that is adjacent an upper end of the stabilisation member 2908 so as to facilitate easier turning of the pins without increasing a central diameter of the pins 2934, thereby reducing space used and allowing a finer adjustment of range of motion of the orthopaedic stabilisation device 100. Further, multiple pins can be used to allow for varying degrees of flexion and extension and, as shown in FIG. 42, adjacent pins 3034 can be arranged in a 'head to toe' configuration so as to prevent interference between adjacent heads of pins 3034.

Figure 43:
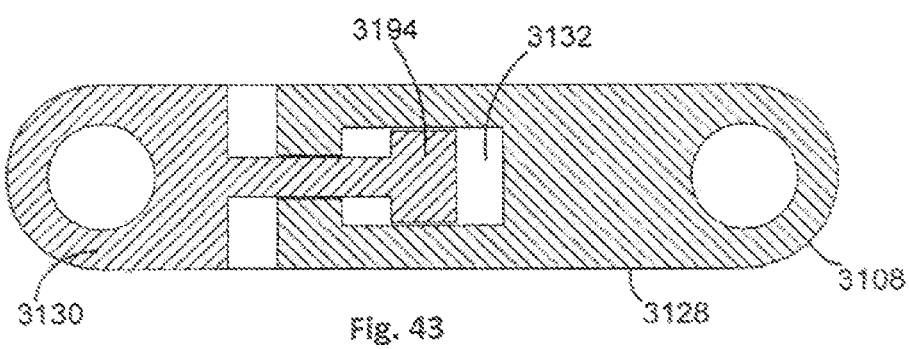
FIG. 43 is a top view of a stabilisation member of an orthopaedic stabilisation device in accordance with an embodiment of the present invention.
Figure 44:
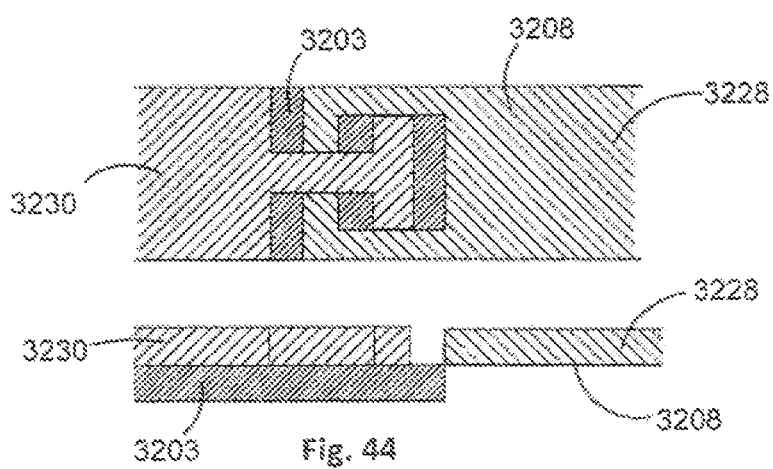
FIG. 44 shows top and side partial cross-sectional views of a stabilisation member of an orthopaedic stabilisation device in accordance with an embodiment of the present invention.

It will be appreciated that other mechanisms can be used to define the motion limits of the orthopaedic stabilisation devices 100, 400. For example, and as shown in FIG. 43, a 'plate-in-plate' arrangement can be used wherein an elongate slot 3132 of a first stabilisation portion 3128 is arranged to receive a plate member 3194 of a second stabilisation portion 3130. The plate member 3194 is constrained to movement within the elongate slot 3132. The first and second stabilisation portions 3128, 3130 can be in the same plane so as to allow for free rotation, or first and second stabilisation portions 3228, 3230 can be mounted with respect to a backing plate 3203 (see FIG. 44) so as to prevent non-axial motion. Clearance between the backing plate 3203 and the first and second stabilisation portions 3228, 3230 can be predefined so as to define an allowable degree of rotation to approximate spinal motion.

Figure 45:
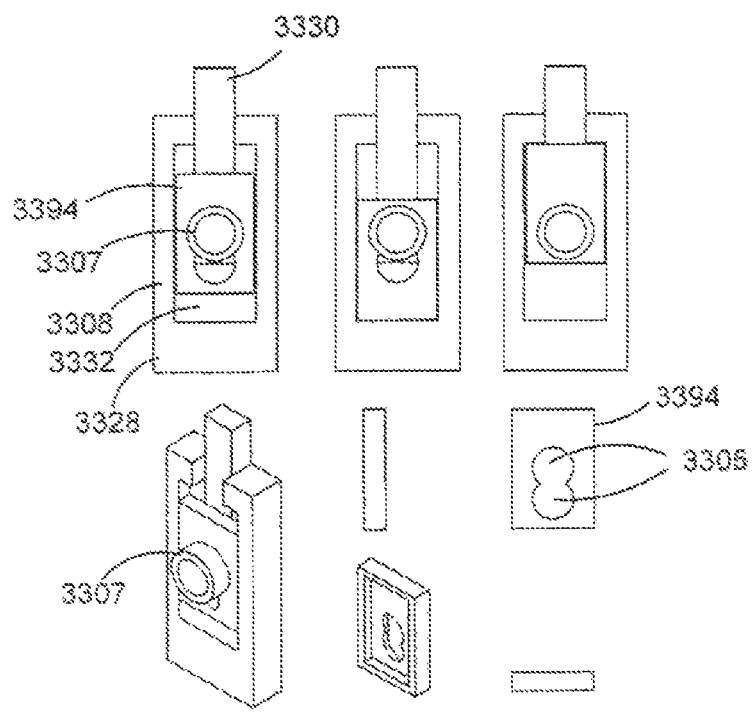
FIG. 45 shows various partial views of a stabilisation member of an orthopaedic stabilisation device in accordance with an embodiment of the present invention.

Referring to a stabilisation member 3308 shown in FIG. 45, a position of a plate member 3394 relative to a second stabilisation member 3330 can be adjustable. The plate member 3394 is received in an elongate slot 3332 of a first stabilisation member 3328, and adjusting the position of the plate member 3394 relative to the second stabilisation member 3330 can allow the stabilisation member 3308 to cater for varying ranges of motion. In this example, the plate member 3394 comprises two apertures 3305 that can receive a clamp member 3307 for clamping the plate member 3394 into a desired position relative to the second stabilisation member 3330.

This can allow the stabilisation member 3308 to be arranged to allow movement corresponding to flexion and/or extension.

Figure 46:
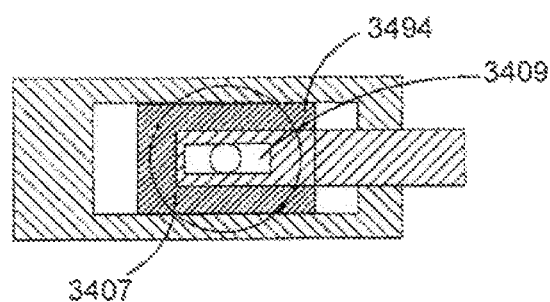
FIG. 46 is a top cross-sectional view of a portion of a stabilisation member of an orthopaedic stabilisation device in accordance with an embodiment of the present invention.
Figure 47A:
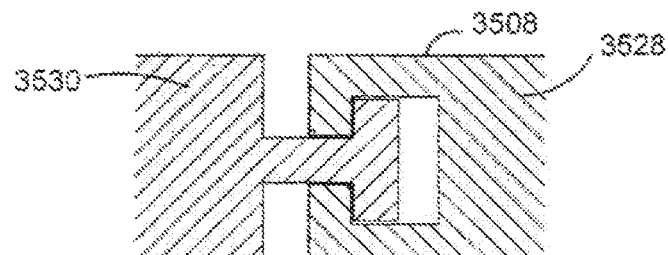
FIGS. 47a and 47b show partial cross-sectional views of stabilisation members of an orthopaedic stabilisation device in accordance with an embodiment of the present invention.
Figure 47B:
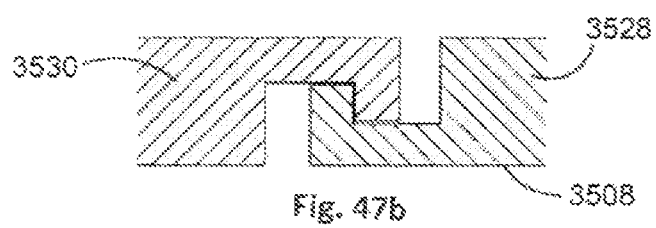

Whereas the example of FIG. 45 shows the plate member 3394 having discretely adjustable positions, FIG. 46 shows an example embodiment wherein a plate member 3494 can be clamped by clamp member 3407 at any desired position along an elongate slot 3409 of the plate member 3494.

It will be appreciated that the 'plate-in-plate' arrangement may be configured such that multiple interference points between first and second stabilisation portions 3528, 3530 of a stabilisation member 3508 are be provided (see FIG. 47a), or wherein a single interference point between the first and second stabilisation portions 3528, 3530 is provided (see FIG. 47b), depending on the requirements for stability of the stabilisation member 3508.

It will be appreciated that the ideal distance between the legs 106 of the orthopaedic stabilisation device 100 may vary depending on the anatomy of the patient. As such, a distance between the legs 106 can be varied, such as by providing an adjustment mechanism or similar, or different orthopaedic stabilisation devices 100 can be provided having different spacing between legs 106.

Figure 48:
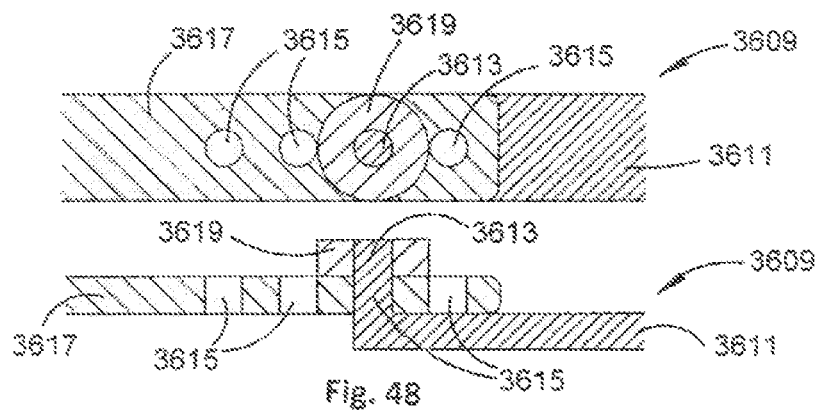
FIG. 48 shows top and side cross-sectional views of a portion of an orthopaedic stabilisation device comprising a length varying mechanism.

As shown in FIG. 48, any appropriate portion 3609 of an orthopaedic stabilisation device can comprise a length varying mechanism that is in series with the motion limit control mechanism and the stiffness control mechanism. In this example, the portion 3609 of the orthopaedic stabilisation device comprises a first spacing portion 3611 comprising a protrusion 3613. The protrusion 3613 is receivable in one of a plurality of apertures 3615 of a second spacing portion 3617, and can be retained by nut 3619. In this example, a length of the orthopaedic stabilisation device, and therefore a spacing between the legs 106, is discretely alterable.

Figure 49:
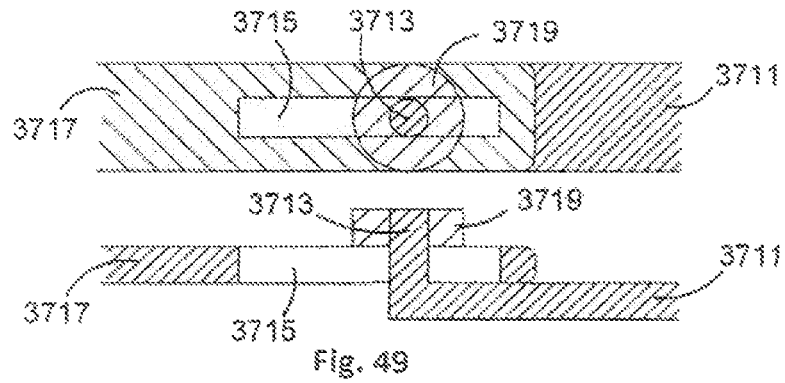
FIG. 49 shows top and side cross-sectional views of a portion of an orthopaedic stabilisation device comprising a length varying mechanism.

An alternative wherein a continuous adjustment of orthopaedic stabilisation device length is provided is shown in FIG. 49. In this example, a protrusion 3713 of a first spacing portion 3711 is receivable in an elongate slot 3715 of a second spacing portion 3717, and is retained by a nut 3719.

Figure 50:
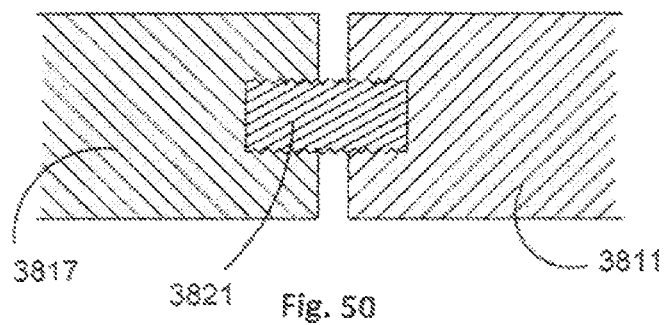
FIG. 50 shows a cross-sectional view of a portion of an orthopaedic stabilisation device comprising a length varying mechanism.

In a further alternative, shown in FIG. 50, a threaded advancement mechanism is used wherein an eccentrically oriented screwdriver can be used to rotate a centrally located thread 3821 that couples first and second spacing portions 3811, 3817 so as to facilitate altering a spacing therebetween.

Often, multiple adjacent intervertebral levels need to be stabilised in a patient. In such cases, multi-level stabilisation can be achieved by either a modular mechanism that allows the introduction or removal of an extra level to a base device, such as the orthopaedic stabilisation devices 100, 400, or by providing multiple orthopaedic stabilisation devices that are capable of stabilising a different number of levels.

Figure 51:
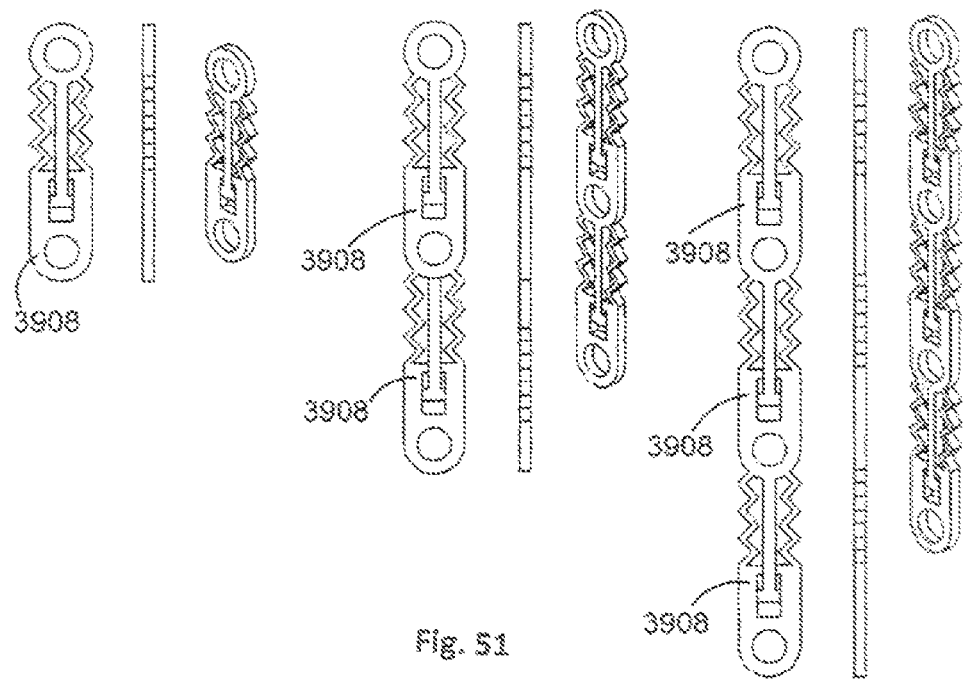
FIG. 51 shows various views of single and multi-level stabilisation members of an orthopaedic stabilisation device in accordance with an embodiment of the present invention.

Examples of multi-level stabilisation devices are illustrated in FIG. 51. In these examples, a plurality of stabilisation members 3908 are coupled together in series. In this case multiple models of the orthopaedic stabilisation device 100 are manufactured and a surgeon can choose the appropriate model.

Figure 52:
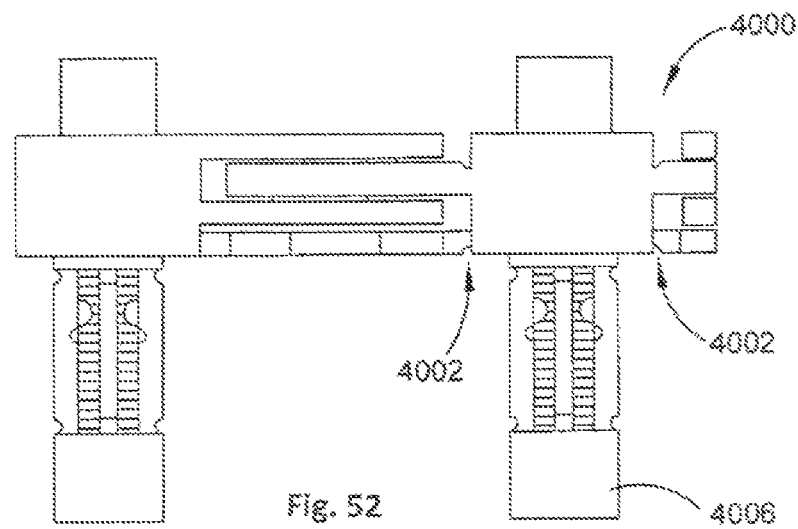
FIG. 52 is a partial side view of an orthopaedic stabilisation device that is arranged to be cut to size in accordance with an embodiment of the present invention.

FIG. 52 shows an example wherein a multi-level orthopaedic stabilisation device 4000 comprises notches 4002 arranged adjacent a leg 4006 to allow a surgeon to remove unnecessary levels by cutting the device 4000 at the notches 4002. For example, a three level orthopaedic stabilisation device can be provided and the surgeon can cut the device down to size as required. This can either be performed using standard surgical tools or a specially designed instrument provided with the orthopaedic stabilisation device 100.

Figure 53:
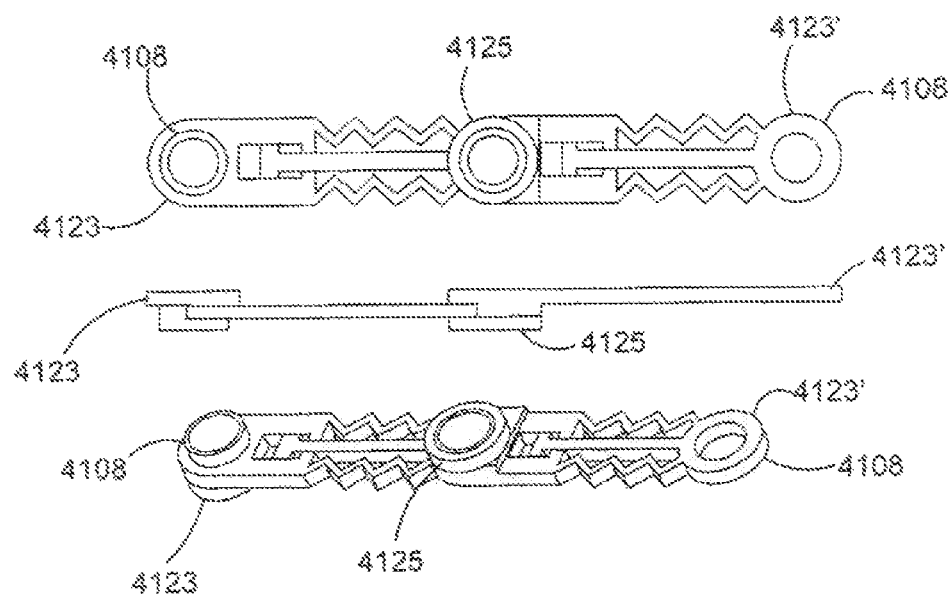
FIG. 53 shows various views of stabilisation members of an orthopaedic stabilisation device in accordance with an embodiment of the present invention, the stabilisation members having a modular design to facilitate coupling the stabilisation members together.

Alternatively, and as shown in FIG. 53, modularity of stabilisation members 4108 can be achieved by providing connectable portions 4123, 4123' that can be coupled together and retained by threaded attachment of a retaining washer 4125.

Implantation of the orthopaedic stabilisation device 100 may be assisted by an awling tool 4200 as shown in FIGS. 54a to 54e. The awling tool comprises two legs 4202 that are coupled by bridging member 4204. Each leg has a frusto-conical end portion 4206 that is arranged to facilitate positioning the awling tool 4200 against bones or bone portions that are to be stabilised by implantation of the orthopaedic stabilisation device 100.

When positioned against the bones or bone portions, a drill or similar can be inserted through respective passages 4208 of each leg to facilitate forming a bore hole in the bones or bone portions. A distance between the respective passages 4208 corresponds to a distance between central axes of the legs 106 of the orthopaedic stabilisation device 100, and therefore the awling tool 4200 can be used to form bore holes that are appropriately spaced to facilitate implantation of each leg 106 into their respective bore holes.

Numerous variations and modifications will suggest themselves to persons skilled in the relevant art, in addition to those already described, without departing from the basic inventive concepts. All such variations and modifications are to be considered within the scope of the present invention, the nature of which is to be determined from the foregoing description.

In the description of the invention, except where the context requires otherwise due to express language or necessary implication, the words "comprise" or variations such as "comprises" or "comprising" are used in an inclusive sense, i.e. to specify the presence of the stated features, but not to preclude the presence or addition of further features in various embodiments of the invention.

The invention claimed is:

1. A fastener for orthopaedic applications and arranged for fastening when positioned in a bore hole in bone, the fastener comprising:
   a head portion; and
   a body that has an axis and that projects from the head portion along the axis, the body including a plurality of body portions each having
      a planar surface extending along and facing away from the axis,
      an actuating surface extending between axial positions along an inner surface of each of the plurality of body portions, the actuating surface being oriented parallel to the planar surface,
      a trapezoidal cross-sectional shape at a base of each of the plurality of body portions of the body, and
      a predefined bending region extending along the planar surface and the actuating surface in the direction of the axis,
   wherein the predefined bending region has parallel inner and outer bending surface portions located at the same axial positions along the axis of the body and that extend along the axial length of the predefined bending region, and
   wherein each of the plurality of body portions bends outwardly within the predefined bending region and is urged away from the axis into the bone when an actuating member is received along the axis and urges against the actuating surface.

2. The fastener of claim 1 wherein each of the plurality of body portions has a polygonal cross-sectional shape in a plane transversal to the axis.

3. The fastener of claim 1 wherein each of the plurality of body portions has a cross-sectional shape that is non-uniform along at least a portion of a length of each of the plurality of body portions.

4. The fastener of claim 3, wherein the cross-sectional shape of each of the plurality of body portions is shaped so as to increase a bending modulus and to allow for expansion of the fastener without plastic deformation.

5. The fastener of claim 1 wherein each of the plurality of body portions projects from the head portion and wherein the body is arranged to move from a contracted to an expanded configuration and wherein the plurality of body portions together have a substantially polygonal cross-sectional profile in a plane perpendicular to the axis of the body, each one of the plurality of body portions corresponding to a respective side of the body and defining an outer portion of the body, the plurality of body portions being arranged such that, when an actuating member is received, the plurality of body portions are urged outwardly so as to move the body to the expanded configuration.

6. The fastener of claim 5 wherein each one of the plurality of body portions is arranged such that, when the body is in the contracted configuration, the plurality of body portions together define a tip at an upper end of the body that can be used to form at least a portion of a bore hole.

7. The fastener of claim 6, wherein each one of the plurality of body portions are separated along at least a portion of a length of the body by a gap, the gap tapering towards the tip of the body.

8. The fastener of claim 5 wherein each one of the plurality of body portions together have a substantially square shaped cross-sectional profile in the plane perpendicular to the axis of the body.

9. The fastener of claim 5 wherein the fastener is arranged such that at least two body portions of the plurality of body portions begin expanding at different times in response to the fastener receiving an actuating member.

10. The fastener of claim 1 wherein the head portion comprises an aperture, the aperture being interconnected with an internal region of the body and being arranged for receiving the actuating member.

11. The fastener of claim 1 wherein at least one external surface of the fastener has a surface that is provided so as to increase friction between the at least one external surface and walls of a bore hole into which the fastener is to be fastened.

12. The fastener of claim 1 wherein each of the plurality of body portions further comprises an engaging portion that is arranged to engage with material into which the fastener is to be fastened, the engaging portion extending in a direction away from the axis.

13. The fastener of claim 1, wherein the actuating surface extends along the axis and along the entire predefined bending region in the direction of the axis.

14. The fastener of claim 1, wherein the planar surface extends along the entire predefined bending region in the direction of the axis.

15. The fastener of claim 1, wherein the fastener elastically deforms when each of the plurality of body portions bends outwardly within the predefined bending region such that deformation of the fastener can be reversed.

* * * * *